US009072738B2

(12) United States Patent
Johnson

(10) Patent No.: US 9,072,738 B2
(45) Date of Patent: Jul. 7, 2015

(54) CHEMICALLY AND METABOLICALLY STABLE DIPEPTIDE POSSESSING POTENT SODIUM CHANNEL BLOCKER ACTIVITY

(75) Inventor: Michael Ross Johnson, Chapel Hill, NC (US)

(73) Assignee: PARION SCIENCES, INC., Durham, NC (US)

( * ) Notice: Subject to any disclaimer, the term of this patent is extended or adjusted under 35 U.S.C. 154(b) by 0 days.

(21) Appl. No.: 14/129,734

(22) PCT Filed: Jun. 27, 2012

(86) PCT No.: PCT/US2012/044372
§ 371 (c)(1),
(2), (4) Date: Jan. 3, 2014

(87) PCT Pub. No.: WO2013/003444
PCT Pub. Date: Jan. 3, 2013

(65) Prior Publication Data
US 2014/0142118 A1      May 22, 2014

Related U.S. Application Data

(60) Provisional application No. 61/501,524, filed on Jun. 27, 2011.

(51) Int. Cl.
| A61K 31/495 | (2006.01) |
| C07D 241/52 | (2006.01) |
| A61K 45/06 | (2006.01) |
| A61K 31/4965 | (2006.01) |
| C07D 241/32 | (2006.01) |
| C07K 5/065 | (2006.01) |

(52) U.S. Cl.
CPC ........... *A61K 31/495* (2013.01); *A61K 31/4965* (2013.01); *A61K 45/06* (2013.01); *C07D 241/32* (2013.01); *C07K 5/06078* (2013.01)

(58) Field of Classification Search
None
See application file for complete search history.

(56) References Cited

U.S. PATENT DOCUMENTS

| 6,858,614 | B2 | 2/2005 | Johnson |
| 6,858,615 | B2 | 2/2005 | Johnson |
| 6,903,105 | B2 | 6/2005 | Johnson |
| 6,995,160 | B2 | 2/2006 | Johnson |
| 7,026,325 | B2 | 4/2006 | Johnson |
| 7,030,117 | B2 | 4/2006 | Johnson |
| 7,064,129 | B2 | 6/2006 | Johnson et al. |
| 7,186,833 | B2 | 3/2007 | Johnson |
| 7,189,719 | B2 | 3/2007 | Johnson |
| 7,192,958 | B2 | 3/2007 | Johnson |
| 7,192,959 | B2 | 3/2007 | Johnson |
| 7,192,960 | B2 | 3/2007 | Johnson |
| 7,241,766 | B2 | 7/2007 | Johnson |
| 7,247,636 | B2 | 7/2007 | Johnson |
| 7,247,637 | B2 | 7/2007 | Johnson et al. |
| 7,317,013 | B2 | 1/2008 | Johnson |
| 7,332,496 | B2 | 2/2008 | Johnson |
| 7,345,044 | B2 | 3/2008 | Johnson |
| 7,368,447 | B2 | 5/2008 | Johnson et al. |
| 7,368,450 | B2 | 5/2008 | Johnson |
| 7,368,451 | B2 | 5/2008 | Johnson et al. |
| 7,375,107 | B2 | 5/2008 | Johnson |
| 7,388,013 | B2 | 6/2008 | Johnson et al. |
| 7,399,766 | B2 | 7/2008 | Johnson |
| 7,410,968 | B2 | 8/2008 | Johnson et al. |
| 7,745,442 | B2 | 6/2010 | Johnson et al. |
| 7,807,834 | B2 | 10/2010 | Johnson et al. |
| 7,820,678 | B2 | 10/2010 | Johnson |

(Continued)

FOREIGN PATENT DOCUMENTS

WO    WO 2005/018644 A1    3/2005

OTHER PUBLICATIONS

U.S. Appl. No. 14/158,441, filed Jan. 17, 2014, Johnson.

(Continued)

*Primary Examiner* — Thomas S Heard
(74) *Attorney, Agent, or Firm* — Oblon, McClelland, Maier & Neustadt, L.L.P.

(57) ABSTRACT

A very stable, selective and renally safe sodium channel blocker represented by the formula: The invention also includes a variety of compositions, combinations and methods of treatment using this inventive sodium channel blocker.

16 Claims, 7 Drawing Sheets

(56) References Cited

U.S. PATENT DOCUMENTS

| | | |
|---|---|---|
| 7,842,697 B2 | 11/2010 | Johnson |
| 7,868,010 B2 | 1/2011 | Johnson et al. |
| 7,875,619 B2 | 1/2011 | Johnson |
| 7,956,059 B2 | 6/2011 | Johnson |
| 7,981,898 B2 | 7/2011 | Johnson et al. |
| 8,008,494 B2 | 8/2011 | Johnson |
| 8,022,210 B2 | 9/2011 | Johnson |
| 8,058,278 B2 | 11/2011 | Johnson et al. |
| 8,124,607 B2 | 2/2012 | Johnson |
| 8,143,256 B2 | 3/2012 | Johnson |
| 8,198,286 B2 | 6/2012 | Johnson |
| 8,211,895 B2 | 7/2012 | Johnson et al. |
| 8,227,474 B2 | 7/2012 | Johnson |
| 8,288,391 B2 | 10/2012 | Johnson et al. |
| 8,314,105 B2 | 11/2012 | Johnson |
| 8,324,218 B2 | 12/2012 | Johnson |
| 8,431,579 B2 | 4/2013 | Johnson et al. |
| 8,507,497 B2 | 8/2013 | Johnson et al. |
| 8,551,534 B2 | 10/2013 | Boucher et al. |
| 8,575,176 B2 | 11/2013 | Johnson |
| 2005/0090505 A1 | 4/2005 | Johnson et al. |
| 2006/0142306 A1 | 6/2006 | Johnson |
| 2007/0265280 A1 | 11/2007 | Johnson |
| 2008/0103148 A1 | 5/2008 | Johnson |
| 2008/0167466 A1 | 7/2008 | Johnson et al. |
| 2008/0176863 A1 | 7/2008 | Johnson et al. |
| 2008/0200476 A1 | 8/2008 | Johnson |
| 2008/0293740 A1 | 11/2008 | Johnson et al. |
| 2009/0018144 A1 | 1/2009 | Johnson et al. |
| 2009/0062308 A1 | 3/2009 | Johnson |
| 2009/0253714 A1 | 10/2009 | Johnson et al. |
| 2009/0324724 A1 | 12/2009 | Johnson |
| 2010/0074881 A1 | 3/2010 | Boucher et al. |
| 2011/0008268 A1 | 1/2011 | Johnson et al. |
| 2011/0195973 A1 | 8/2011 | Johnson |
| 2013/0012692 A1 | 1/2013 | Johnson |
| 2013/0060034 A1 | 3/2013 | Johnson |
| 2013/0178482 A1 | 7/2013 | Johnson |
| 2013/0324559 A1 | 12/2013 | Johnson et al. |
| 2014/0031371 A1 | 1/2014 | Johnson |

OTHER PUBLICATIONS

U.S. Appl. No. 14/047,281, Johnson.
U.S. Appl. No. 14/132,194, Johnson.
U.S. Appl. No. 14/106,098, filed Dec. 13, 2013, Johnson.
U.S. Appl. No. 14/106,125, filed Dec. 13, 2013, Johnson.
Qadri, Y. J. et al., "Amiloride Docking to Acid-Sensing Ion Channel-1", The Journal of Biological Chemistry, vol. 285, No. 13, pp. 9627-9635, (Mar. 26, 2010).
International Search Report Issued Sep. 6, 2012 in PCT/US12/044372 Filed Jun. 27, 2012.
U.S. Appl. No. 14/106,156, filed Dec. 13, 2013, Johnson.
Combined Chinese Office Action and Search Report issued Aug. 12, 2014 in Patent Application No. 201280031699.7 (with English language translation).
U.S. Appl. No. 14/458,898, filed Aug. 13, 2014, Johnson, et al.
Extended European Search Report issued Oct. 15, 2014 in Patent Application No. 12803924.5.
Communication pursuant to Rules 70(2) and 70a(2) EPC issued Oct. 31, 2014 in European Patent Application No. 12803924.5.

CHEMICALLY AND METABOLICALLY STABLE DIPEPTIDE POSSESSING POTENT SODIUM CHANNEL BLOCKER ACTIVITY

The present application claims priority to U.S. Ser. No. 61/501,524, filed Jun. 27, 2011, the entire contents of which are hereby incorporated herein by reference.

BACKGROUND OF THE INVENTION

1. Field of the Invention

The present invention relates to epithelial sodium channel blocker 3,5-diamino-6-chloro-N—(N-(4-(4-((S)-3-(dimethylamino)-4-((S)-1-(dimethylamino)-6-guanidino-1-oxohexan-2-ylamino)-4-oxobutyl)phenyl)butyl)carbamimidoyl) pyrazine-2-carboxamide (I). The present invention also includes a variety of methods of treatment using this inventive sodium channel blocker. The present invention also relates to novel compounds for the treatment of dry eye, particularly including 3,5-diamino-6-chloro-N—(N-(4-(4-((S)-3-(dimethylamino)-4-((S)-1-(dimethylamino)-6-guanidino-1-oxohexan-2-ylamino)-4-oxobutyl)phenyl)butyl)carbamimidoyl) pyrazine-2-carboxamide (I) and its pharmaceutically acceptable salt forms, useful as sodium channel blockers, compositions containing the same, therapeutic methods and uses for the same and processes for preparing the same.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion (Cl$^-$ and/or HCO$_3^-$) secretion coupled with water (and a cation counter-ion), and epithelial liquid absorption, often reflecting Na$^+$ absorption, coupled with water and counter anion (Cl$^-$ and/or HCO$_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking Na$^+$ channel and liquid absorption. The epithelial protein that mediates the rate-limiting step of Na$^+$ and liquid absorption is the epithelial Na$^+$ channel (ENaC). ENaC is positioned on the apical surface of the epithelium, i.e. the mucosal surface-environmental interface. Therefore, to inhibit ENaC mediated Na$^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic obstructive pulmonary diseases are characterized by dehydration of airway surfaces and the retention of mucous secretions in the lungs. Examples of such diseases include cystic fibrosis, chronic bronchitis, and primary or secondary ciliary dyskinesia. Such diseases affect approximately 15 million patients in the United States, and are the sixth leading cause of death. Other airway or pulmonary diseases characterized by the accumulation of retained mucous secretions include sinusitis (an inflammation of the paranasal sinuses associated with upper respiratory infection) and pneumonia.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

R. C. Boucher, in U.S. Pat. No. 6,926,911, suggests the use of the relatively impotent sodium channel blockers such as amiloride, with osmolytes for the treatment of airway diseases. This combination gives no practical advantage over either treatment alone and is clinically not useful, see Donaldson et al, N Eng J Med., 2006; 353:241-250. Amiloride was found to block the water permeability of airways and negate the potential benefit of concurrent use of hypertonic saline and amiloride.

U.S. Pat. No. 5,817,028 to Anderson describes a method for the provocation of air passage narrowing (for evaluating susceptibility to asthma) and/or the induction of sputum in subjects via the inhalation of mannitol. It is suggested that the same technique can be used to induce sputum and promote mucociliary clearance. Substances suggested include sodium chloride, potassium chloride, mannitol and dextrose.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity.

Similarly, keratoconjunctivitis sira (dry eye) is caused by failure of lacrimal glands to secrete liquid in the face of continued $Na^+$ dependent liquid absorption on conjunctional surfaces. Keratoconjunctivitis sicca (KCS) or chronic dry eye disease (DED) is one of the most frequently diagnosed ocular diseases, resulting in painful irritation, inflammation on the ocular surface, and impaired vision. KCS/DED results from inadequate aqueous tear fluid on the eyes. Dry eye is one of the most frequently diagnosed ocular diseases affecting more than 5 million people in the United States alone. Dry eye is a multi-factorial disease, resulting from a common etiology of insufficient tear film causing ocular surface damage and symptoms of ocular discomfort. The few current therapies available, which include immunosuppressive agents and over-the-counter tear replacements, are not sufficiently efficacious for many users or only provide transient relief from dry eye symptoms. Therefore, the development of novel agents to treat dry eye would be of tremendous benefit to the therapeutic milieu. The volume of tear film on the ocular surface represents a balance between tear fluid output versus fluid loss via drainage, evaporation, or epithelial absorption. Similar to other epithelial tissues, the epithelium of the conjunctiva and cornea are capable of regulating the hydration status of the mucosal surface through active salt and water transport. The epithelial sodium channel (ENaC) is a key regulator of sodium (and water) absorption in numerous tissues including the eye. The inhibition of ENaC in the eye is predicted to preserve lacrimal secretions and maintain hydration on the ocular surface.

In rhinosinusitis, there is an imbalance, as in CB, between mucin secretion and relative ASL depletion. Finally, in the gastrointestinal tract, failure to secrete Cl− (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

The published literature includes a number of patent applications and granted patents to Parion Sciences Inc., directed toward pyrazinoylguanidine analogs as sodium channel blockers. Examples of such publications include PCT Publication Nos. WO2003/070182, WO2003/070184, WO2004/073629, WO2005/025496, WO2005/016879, WO2005/018644, WO2006/022935, WO2006/023573, WO2006/023617, WO2007/018640, WO2007/146869, WO2008/031028, WO2008/031048, and U.S. Pat. Nos. 6,858,614, 6,858,615, 6,903,105, 7,064,129, 7,186,833, 7,189,719, 7,192,958, 7,192,959, 7,192,960, 7,241,766, 7,247,636, 7,247,637, 7,317,013, 7,332,496, 7,368,447, 7,368,450, 7,368,451, 7,375,102, 7,388,013, 7,399,766, 7,410,968, 7,807,834, 7,842,697, and 7,868,010.

There remains a need for novel sodium channel blocking compounds with enhanced potency and effectiveness on mucosal tissues. There also remains the need for novel sodium channel blocking compounds that provide therapeutic effect, but minimize or eliminate the onset or progression of hyperkalemia in recipients.

SUMMARY OF THE INVENTION

It is an object of the present invention to provide a compound that is stable in liquid formulations suitable for topical administration.

It is an object of the present invention to provide a compound that is more potent in vivo and/or absorbed less rapidly from mucosal surfaces, and/or are less reversible as compared to known compounds such as amiloride, benzamil and phenamil.

It is another object of the present invention to provide compounds which are (1) absorbed less rapidly from mucosal surfaces, especially airway surfaces, as compared to known compounds and; (2) when absorbed from musosal surfaces after administration to the mucosal surfaces, are largely non renally absorbed so as to prevent renal side effects such as hyperkalemia.

It is another object of the present invention to provide methods of treatment that take advantage of the pharmacological properties of the compounds described above.

In particular, it is an object of the present invention to provide methods of treatment which rely on rehydration of mucosal surfaces.

In particular, it is an object of the present invention to provide methods of treating dry eye and related ocular diseases.

The objects of the present invention may be accomplished with a pyrazinoylguanidine represented by the compound of formula (I):

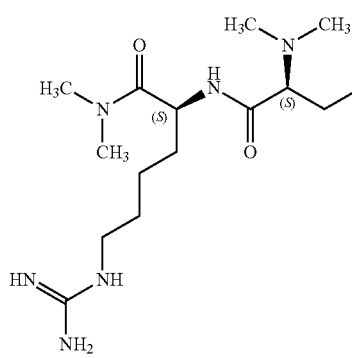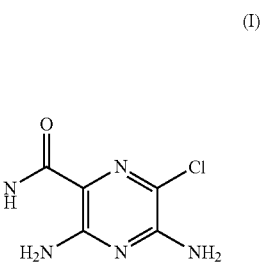

(I)

The present invention also provides pharmaceutical compositions which comprise the compound described herein.

The present invention also provides a method of promoting hydration of mucosal surfaces, comprising:
administering an effective amount of compound I described herein to a mucosal surface of a subject.

The present invention also provides a method of restoring mucosal defense, comprising:
topically administering an effective amount compound I described herein to a mucosal surface of a subject in need thereof.

The present invention also provides a method of blocking ENaC, comprising:
contacting sodium channels with an effective amount of compound I represented by described herein.

The present invention also provides a method of promoting mucus clearance in mucosal surfaces, comprising:
administering an effective amount of compound I described herein to a mucosal surface of a subject.

The present invention also provides a method of treating chronic bronchitis, comprising:
administering an effective amount of compound I described herein to a subject in need thereof.

The present invention also provides a method of treating cystic fibrosis, comprising:
administering an effective amount of compound I described herein to a subject in need thereof.

The present invention also provides a method of treating rhinosinusitis, comprising:
administering an effective amount of compound I described herein to a subject in need thereof.

The present invention also provides a method of treating nasal dehydration, comprising:
administering an effective amount of compound I described herein to the nasal passages of a subject in need thereof.

In a specific embodiment, the nasal dehydration is brought on by administering dry oxygen to the subject.

The present invention also provides a method of treating sinusitis, comprising:
administering an effective amount of compound I described herein to a subject in need thereof.

The present invention also provides a method of treating pneumonia, comprising:
administering an effective amount of compound I described herein to a subject in need thereof.

The present invention also provides a method of treating ventilator-induced pneumonia, comprising:
administering an effective amount of compound I described herein to a subject by means of a ventilator.

The present invention also provides a method of treating asthma, comprising:
administering an effective amount of compound I described herein to a subject in need thereof.

The present invention also provides a method of treating primary ciliary dyskinesia, comprising:
administering an effective amount of compound I described herein to a subject in need thereof.

The present invention also provides a method of treating otitis media, comprising:
administering an effective amount of compound I described herein to a subject in need thereof.

The present invention also provides a method of inducing sputum for diagnostic purposes, comprising:
administering an effective amount of compound I described herein to a subject in need thereof.

The present invention also provides a method of treating chronic obstructive pulmonary disease, comprising:
administering an effective amount of compound I described herein to a subject in need thereof.

The present invention also provides a method of treating emphysema, comprising:
administering an effective amount of compound I described herein to a subject in need thereof.

The present invention also provides a method of treating dry eye, comprising:
administering an effective amount of compound I described herein to the eye of the subject in need thereof.

The present invention also provides a method of promoting ocular hydration, comprising:
administering an effective amount of compound I described herein to the eye of the subject.

The present invention also provides a method of promoting corneal hydration, comprising:
administering an effective amount of compound I described herein to the eye of the subject.

The present invention also provides a method of treating Sjögren's disease, comprising:
administering an effective amount of compound I described herein to a subject in need thereof.

The present invention also provides a method of treating vaginal dryness, comprising:
administering an effective amount of compound I described herein to the vaginal tract of a subject in need thereof.

The present invention also provides a method of treating dry skin, comprising:

administering an effective amount of compound I described herein to the skin of a subject in need thereof.

The present invention also provides a method of treating dry mouth (xerostomia), comprising:
administering an effective amount of compound I described herein to the mouth of the subject in need thereof.

The present invention also provides a method of treating distal intestinal obstruction syndrome, comprising:
administering an effective amount of compound I described herein to a subject in need thereof.

The present invention also provides a method of treating esophagitis, comprising:
administering an effective amount of compound I described herein to a subject in need thereof.

The present invention also provides a method of treating bronchiectasis, comprising:
administering an effective amount of compound I described herein to a subject in need thereof.

The present invention also provides a method of treating constipation, comprising:
administering an effective amount of compound I described herein to a subject in need thereof. In one embodiment of this method, the compound is administered either orally or via a suppository or enema.

The present invention also provides a method of treating chronic diverticulitis comprising:
administering an effective amount of compound I described herein to a subject in need thereof.

It is another aspect of the present invention to provide treatments using the sodium channel blocker when administered with an osmotic enhancer. Therefore, such a sodium channel blocker of Formula I when used in conjunction with osmolytes will give a prolonged pharmacodynamic half-life on mucosal surfaces as compared to either compound used alone.

It is another object of the present invention to provide treatments using a sodium channel blocker of formula (I) and osmolytes together which are absorbed less rapidly from mucosal surfaces, especially airway surfaces.

It is another object of the invention to provide compositions which contain a sodium channel blocker of formula (I) and osmolytes.

The objects of the invention may be accomplished with a method of treating a disease ameliorated by increased mucociliary clearance and mucosal hydration comprising administering an effective amount of the compound of formula (I) as defined herein and an osmolyte to a subject to a subject in need of increased mucociliary clearance and mucosal hydration.

The objects of the invention may also be accomplished with a method of inducing sputum for diagnostic purposes, comprising administering an effective amount of the compound of formula (I) as defined herein and an osmolyte to a subject in need thereof.

The objects of the invention may also be accomplished with a method of treating anthrax, comprising administering an effective amount of the compound of formula (I) as defined herein and an osmolyte to a subject in need thereof.

The objects of the invention may also be accomplished with a method of prophylactic, post-exposure prophylactic, preventive or therapeutic treatment against diseases or conditions caused by pathogens, particularly pathogens which may be used in bioterrorism, comprising administering an effective amount of the compound of formula (I) to a subject in need thereof.

The objects of the invention may also be accomplished with a composition, comprising the compound of formula (I) as defined herein and an osmotically active compound.

DESCRIPTION OF THE FIGURES

FIG. 4. The Effects of 10 mM P-1046 (Formula I, 15) on Tear Output in ExLac Rats. The raw PRT tear output values are shown in the left panel and the baseline corrected values are shown in the right panel. A single 10 mM dose of P-1046 produces increased tear volume relative to vehicle controls. While the raw tear output data are not significant beyond 60 minutes (reflecting the higher baseline values for control animals relative to P-1046 treated animals), the baseline corrected data are statistically significant at all post-dose time points (p<0.03) n=3 for both groups.

DETAILED DESCRIPTION OF THE INVENTION

Figure 1:
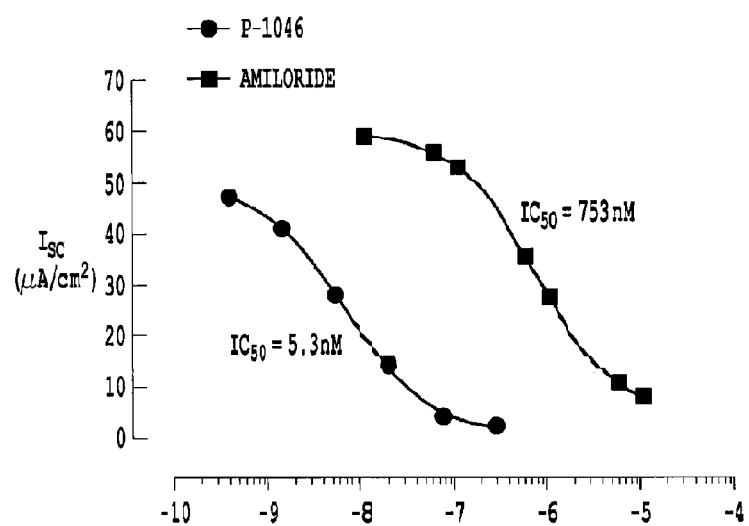
FIG. 1: Dose Response Curve of ENaC Inhibition with P-1046 (I) and Amiloride. The potency of P-1046 compared to amiloride was generated in Ussing chamber studies using primary cultures of canine bronchial epithelial cells. P-1046 is >100-fold more potent than amiloride as indicated by the leftward shift in the dose response curve.

The present invention is based on the discovery that the compound of formula (I) is more potent and/or absorbed less rapidly from mucosal surfaces, especially airway surfaces, compared to known sodium channel blockers such as amilorde, benzamil, and phenamil. Therefore, the compound of formula (I) has a longer half-life on mucosal surfaces as compared to these compounds.

The present invention is also based on the discovery that certain compounds embraced by formula (I) are (1) absorbed less rapidly from mucosal surfaces, especially ocular surfaces, as compared to known compounds and (2) when absorbed from musosal surfaces after administration to the mucosal surfaces, are excreted mainly non-renally in order to minimize the chances of hyperkalemia.

The present invention is also based on the discovery that certain compounds embraced by formula (I) provide methods of treatment that take advantage of the pharmacological properties of the compounds described above.

In particular, the present invention is also based on the discovery that certain compounds embraced by formula (I) rehydrate of mucosal surfaces.

In particular, the present invention is also based on the discovery that certain compounds embraced by formula (I) are useful in treating dry eye and related ocular diseases.

Compound I described herein may be prepared and used as the free base. Alternatively, the compound may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures, tautomers, polymorphs, pseudopolymorphs and pharmaceutically acceptable salts of the compound within the scope of formula (I) are embraced by the present invention. All mixtures of such enantiomers and diastereomers are within the scope of the present invention.

A compound of formula I and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of formula I and their pharmaceutically acceptable salts.

A compound of formula I and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of formula I-III and their pharmaceutically acceptable salts.

The compound of formula I may exist in different tautomeric forms. One skilled in the art will recognize that guanidines can exist in tautomeric forms. By way of example and not by way of limitation, compounds of formula I can exist in various tautomeric forms as shown below:

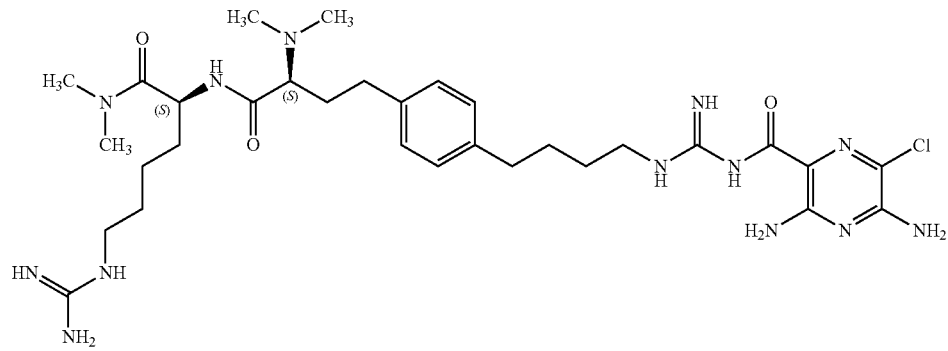

-continued

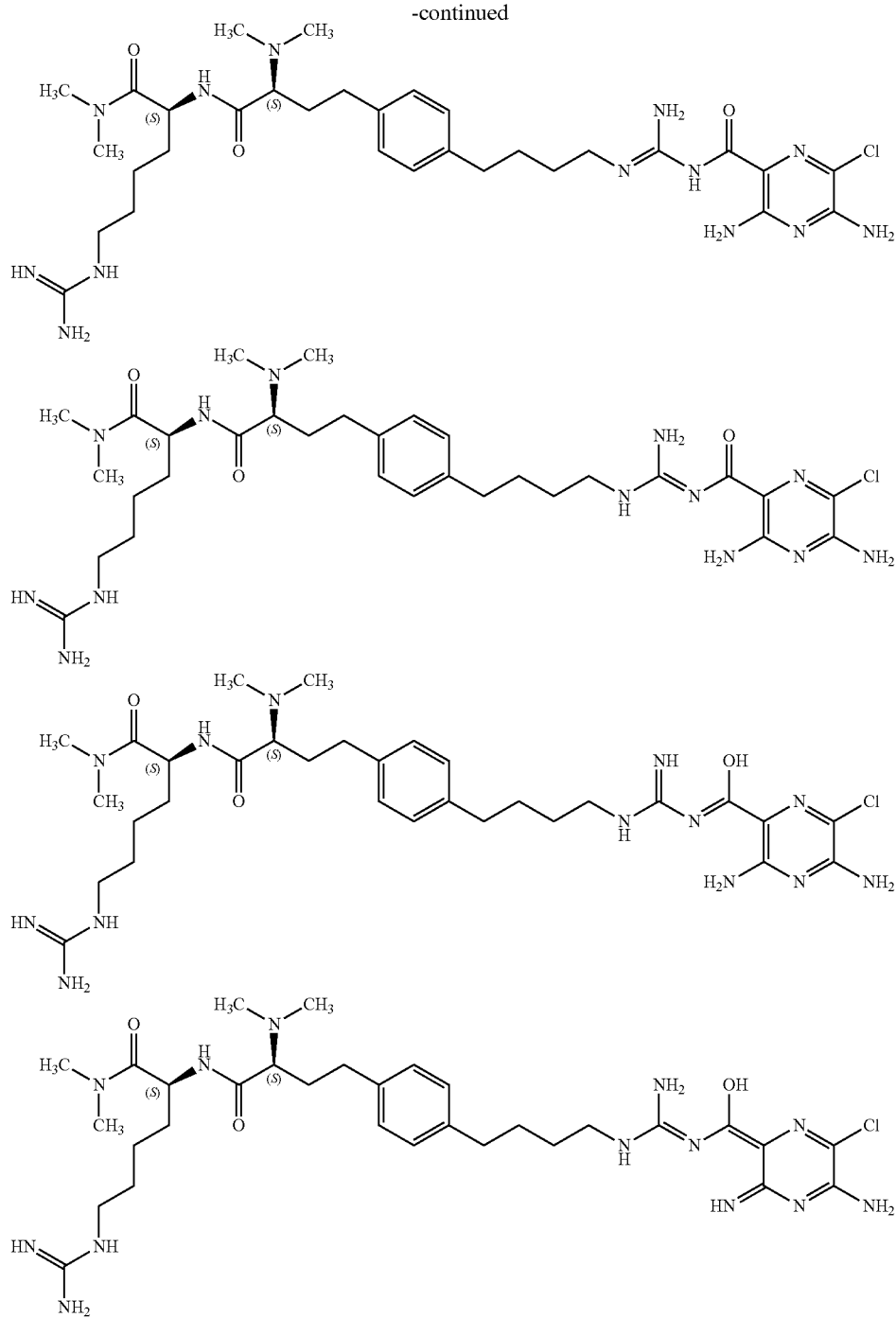

All possible tautomeric forms of the guanidines and acyl guanidines all of the embodiments of formula I are within the scope of the instant invention.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and 1, D and L, or (+) and (−) are employed to designate the sign of rotation of plane-polarized light by the compound, with S, (−), or 1 meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.,* 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

The term "diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

Without being limited to any particular theory, it is believed that the compound of formula (I) in vivo as sodium channel blockers. By blocking epithelial sodium channels present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds described herein as discussed above. Thus, subjects that may be treated by the methods of the present invention include, but are not limited to, patients afflicted with cystic fibrosis, primary ciliary dyskinesia, chronic bronchitis, bronchiectasis chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., *staphylococcus* infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genitourethral surfaces, ocular surfaces or surfaces of the eye, the inner ear and the middle ear. For example, the active compounds of the present invention may be administered by any suitable means, including locally/topically, orally, or rectally, in an effective amount.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

Without being limited to any particular theory, it is believed that sodium channel blockers of the present invention block epithelial sodium channels present in mucosal surfaces the sodium channel blocker, described herein reduce the absorption of salt and water by the mucosal surfaces. This effect increases the volume of protective liquids on mucosal surfaces, rebalances the system, and thus treats disease. This effect is enhanced when used in combination with osmolytes.

The compounds of formula (I) may also be used in conjunction with osmolytes thus lowering the dose of the compound needed to hydrate mucosal surfaces. This important property means that the compound will have a lower tendency to cause undesired side-effects by blocking sodium channels located at untargeted locations in the body of the recipient, e.g., in the kidneys when used in combination with an osmolyte.

Active osmolytes of the present invention are molecules or compounds that are osmotically active (i.e., are "osmolytes"). "Osmotically active" compounds of the present invention are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention. It is to be noted that all racemates, enantiomers, diastereomers, tautomers, polymorphs and pseudopolymorphs and racemic mixtures of the osmotically active compounds are embraced by the present invention.

Active osmolytes useful in the present invention that are ionic osmolytes include any salt of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., *Remington: The Science and Practice of Pharmacy, Vol. II*, pg. 1457 (19th Ed. 1995), incorporated herein by reference, and can be used in any combination including their conventional combinations.

Pharmaceutically acceptable osmotically active anions that can be used to carry out the present invention include, but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrte, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include chloride, sulfate, nitrate, gluconate, iodide, bicarbonate, bromide, and phosphate.

Pharmaceutically acceptable cations that can be used to carry out the present invention include, but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the present invention include but are not limited to aluminum, calcium, lithium, magnesium, potassium, sodium, zinc, iron, ammonium, and the like. Particularly preferred cations include sodium, potassium, choline, lithium, meglumine, D-lysine, ammonium, magnesium, and calcium.

Specific examples of osmotically active salts that may be used with the sodium channel blockers described herein to carry out the present invention include, but are not limited to, sodium chloride, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, etc. Either a single salt or a combination of different osmotically active salts may be used to carry out the present invention. Combinations of different salts are preferred. When different salts are used, one of the anion or cation may be the same among the differing salts.

Osmotically active compounds of the present invention also include non-ionic osmolytes such as sugars, sugar-alcohols, and organic osmolytes. Sugars and sugar-alcohols useful in the practice of the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol useful in the present invention are also active compounds within the scope of the invention. For example, glucose, when reduced, becomes sorbitol; within the scope of the invention, sorbitol and other reduced forms of sugar/sugar alcohols (e.g., mannitol, dulcitol, arabitol) are accordingly active compounds of the present invention.

Osmotically active compounds of the present invention additionally include the family of non-ionic osmolytes termed "organic osmolytes." The term "organic osmolytes" is generally used to refer to molecules used to control intracellular osmolality in the kidney. See e.g., J. S. Handler et al., *Comp. Biochem. Physiol,* 117, 301-306 (1997); M. Burg, *Am. J. Physiol.* 268, F983-F996 (1995), each incorporated herein by reference. Although the inventor does not wish to be bound to any particular theory of the invention, it appears that these organic osmolytes are useful in controlling extracellular volume on the airway/pulmonary surface. Organic osmolytes useful as active compounds in the present invention include but are not limited to three major classes of compounds: polyols (polyhydric alcohols), methylamines, and amino acids. The polyol organic osmolytes considered useful in the practice of this invention include, but are not limited to, inositol, myo-inositol, and sorbitol. The methylamine organic osmolytes useful in the practice of the invention include, but are not limited to, choline, betaine, carnitine (L-, D- and DL forms), phosphorylcholine, lyso-phosphorylcholine, glycerophosphorylcholine, creatine, and creatine phosphate. The amino acid organic osmolytes of the invention include, but are not limited to, the D- and L-forms of glycine, alanine, glutamine, glutamate, aspartate, proline and taurine. Additional osmolytes useful in the practice of the invention include tihulose and sarcosine. Mammalian organic osmolytes are preferred, with human organic osmolytes being most preferred. However, certain organic osmolytes are of bacterial, yeast, and marine animal origin, and these compounds are also useful active compounds within the scope of the present invention.

Under certain circumstances, an osmolyte precursor may be administered to the subject; accordingly, these compounds are also useful in the practice of the invention. The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or pro-drugs and are known in the art. (See, for example, U.S. Pat. Nos. 4,479,932 and 4,540,564; Shek, E. et al., *J. Med. Chem.*

19:113-117 (1976); Bodor, N. et al., *J. Pharm. Sci.* 67:1045-1050 (1978); Bodor, N. et al., *J. Med. Chem.* 26:313-318 (1983); Bodor, N. et al., *J. Pharm. Sci.* 75:29-35 (1986), each incorporated herein by reference.

In general, osmotically active compounds of the present invention (both ionic and non-ionic) that do not promote, or in fact deter or retard bacterial growth are preferred.

The compounds of formula (I) described herein and osmotically active compounds disclosed herein may be administered in any order and/or concurrently to mucousal surfaces such as the eye, the nose, and airway surfaces including the nasal passages, sinuses and lungs of a subject by any suitable means known in the art, such as by nose drops, mists, aerosols, continuous overnight nasal cannulation, etc. In one embodiment of the invention, the compounds of formula (I) and osmotically active compounds of the present invention are administered concurrently by transbronchoscopic lavage. In a preferred embodiment of the invention, the compounds of formula (I) and osmotically active compounds of the present invention are deposited on lung airway surfaces by administering by inhalation an respirable aerosol respirable particles comprised of the compounds of formula (I) and the osmotically active compounds, in which the compounds of formula (I) can precede or follow the independent delivery of an osmotically active compound within a sufficiently short time for their effects to be additive. The respirable particles may be liquid or solid. Numerous inhalers for administering aerosol particles to the lungs of a subject are known. In another preferred embodiment of the invention, the compounds of formula (I) and osmotically active compounds can be given concurrently as defined herein.

The compounds of formula (I) and osmotically active compounds of the present invention are administered sequentially (in any order) or concurrently to the subject in need thereof. As used herein, the term "concurrently" means sufficiently close in time to produce a combined effect (that is, concurrently may be simultaneously, or it may be two or more events occurring within a short time period before or after each other). Concurrently also embraces the delivery of the compounds of formula (I) and osmolytes as a mixture or solution of the two components as well as when delivered from two different nebulizers. An example of that would be the delivery of compound 1 in one nebulizer and hypertonic saline in a second nebulizer connected by a T-piece. When administered with other active agents, the active compounds of the present invention may function as a vehicle or carrier for the other active agent, or may simply be administered concurrently with the other active agent. The active compound of the present invention may be used as a dry or liquid vehicle for administering other active ingredients to airway surfaces. Such other active agents may be administered for treating the disease or disorder for which they are intended, in their conventional manner and dosages, in combination with the active compounds of the present invention, which may be thought of as serving as a vehicle or carrier for the other active agent. Any such other active ingredient may be employed, particularly where hydration of the airway surfaces (i.e., the activity of the osmotically active compounds of the present invention) facilitates the activity of the other active ingredient (e.g., by facilitating or enhancing uptake of the active ingredient, by contributing to the mechanism of action of the other active ingredient, or by any other mechanisms). In a preferred embodiment of the invention, when the active compound of the present invention is administered concurrently with another active agent, the active compound of the present invention has an additive effect in relation to the other active agent; that is, the desired effect of the other active agent is enhanced by the concurrent administration of the active compounds of the present invention.

The compounds of formula (I) of the present invention are also useful for treating airborne infections. Examples of airborne infections include, for example, RSV. The compounds of formula (I) of the present invention are also useful for treating an anthrax infection. The present invention relates to the use of the compounds of formula (I) of the present invention for prophylactic, post-exposure prophylactic, preventive or therapeutic treatment against diseases or conditions caused by pathogens. In a preferred embodiment, the present invention relates to the use of the compounds of formula (I) for prophylactic, post-exposure prophylactic, preventive or therapeutic treatment against diseases or conditions caused by pathogens which may be used in bioterrorism.

In recent years, a variety of research programs and biodefense measures have been put into place to deal with concerns about the use of biological agents in acts of terrorism. These measures are intended to address concerns regarding bioterrorism or the use of microorganisms or biological toxins to kill people, spread fear, and disrupt society. For example, the National Institute of Allergy and Infectious Diseases (NIAID) has developed a Strategic Plan for Biodefense Research which outlines plans for addressing research needs in the broad area of bioterrorism and emerging and reemerging infectious diseases. According to the plan, the deliberate exposure of the civilian population of the United States to *Bacillus anthracis* spores revealed a gap in the nation's overall preparedness against bioterrorism. Moreover, the report details that these attacks uncovered an unmet need for tests to rapidly diagnose, vaccines and immunotherapies to prevent, and drugs and biologics to cure disease caused by agents of bioterrorism.

Much of the focus of the various research efforts has been directed to studying the biology of the pathogens identified as potentially dangerous as bioterrorism agents, studying the host response against such agents, developing vaccines against infectious diseases, evaluating the therapeutics currently available and under investigation against such agents, and developing diagnostics to identify signs and symptoms of threatening agents. Such efforts are laudable but, given the large number of pathogens which have been identified as potentially available for bioterrorism, these efforts have not yet been able to provide satisfactory responses for all possible bioterrorism threats. Additionally, many of the pathogens identified as potentially dangerous as agents of bioterrorism do not provide adequate economic incentives for the development of therapeutic or preventive measures by industry. Moreover, even if preventive measures such as vaccines were available for each pathogen which may be used in bioterrorism, the cost of administering all such vaccines to the general population is prohibitive.

Until convenient and effective treatments are available against every bioterrorism threat, there exists a strong need for preventative, prophylactic or therapeutic treatments which can prevent or reduce the risk of infection from pathogenic agents.

The present invention provides such methods of prophylactic treatment. In one aspect, a prophylactic treatment method is provided comprising administering a prophylactically effective amount of the compounds of formula (I) to an individual in need of prophylactic treatment against infection from one or more airborne pathogens. A particular example of an airborne pathogen is anthrax.

In another aspect, a prophylactic treatment method is provided for reducing the risk of infection from an airborne pathogen which can cause a disease in a human, said method comprising administering an effective amount of the compounds of formula (I) to the lungs of the human who may be at risk of infection from the airborne pathogen but is asymptomatic for the disease, wherein the effective amount of a sodium channel blocker and osmolye are sufficient to reduce the risk of infection in the human. A particular example of an airborne pathogen is anthrax.

In another aspect, a post-exposure prophylactic treatment or therapeutic treatment method is provided for treating infection from an airborne pathogen comprising administering an effective amount of the compounds of formula (I) to the lungs of an individual in need of such treatment against infection from an airborne pathogen. The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism. The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality. Particular examples of these pathogens are anthrax and plague. Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656, 256, and U.S. Pat. No. 5,292,498, each of which is incorporated herein by reference.

Bronchodiloators can also be used in combination with compounds of the present invention. These bronchodilators include, but are not limited to, β-adrenergic agonists including but not limited to epinephrine, isoproterenol, fenoterol, albutereol, terbutalin, pirbuterol, bitolterol, metaproterenol, isoetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 µm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by a suitable means know in the art, such as by nose drops, mists, etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer (L C Star) or an ultrasonic nebulizer (Pari eFlow). See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^{4}$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 (19$^{th}$ ed. 1995), incorporated herein by reference. Pharmaceutical formulations suitable for nasal administration may be prepared as described in U.S. Pat. No. 4,389,393 to Schor; U.S. Pat. No. 5,707,644 to Ilium; U.S. Pat. No. 4,294,829 to Suzuki; and U.S. Pat. No. 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compound of formula I may be synthesized according to procedures known in the art. A representative synthetic procedure is shown in the scheme below:

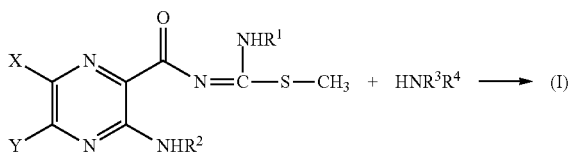

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Additional methods of preparing intermediates used in the preparation of compounds of the instant invention are disclosed in U.S. Pat. No. 7,064,129, U.S. Pat. No. 6,858,615, U.S. Pat. No. 6,903,105, WO 2004/073629, WO 2007/146869, and WO 2007/018640, each of which is expressly incorporated by reference.

Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1 \times 10^{-11}$ M to $3 \times 10^{-5}$ M), and the cumulative change in $I_{sc}$ (inhibition) recorded. All drugs are prepared in dimethyl sulfoxide as stock solutions at a concentration of $1 \times 10^{-2}$ M and stored at $-20°$ C. Eight preparations are typically run in parallel; two preparations per run incorporate amiloride and/or benzamil as positive controls. After the maximal concentration ($5 \times 10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls. The potency of the sodium channel blocking activity of representative compounds in freshly excised cell from canine airways is shown in Table 2.

TABLE 2

| In Vitro Measure of Sodium Channel Blocking Activity | |
| --- | --- |
| Compound | $IC_{50}$ (nM) |
| I | 5.3 |
| amiloride | 781 |

Pharmacological Assays of Absorption
(1) Apical Disappearance Assay

Bronchial cells (dog, human, sheep, or rodent cells) are seeded at a density of $0.25 \times 10^6/cm^2$ on a porous Transwell-Col collagen-coated membrane with a growth area of 1.13 $cm^2$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_t$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 µl) and is initiated by adding experimental sodium channel blockers or positive controls (amiloride, benzamil, phenamil) to the apical surface at an initial concentration of 10 µM. A series of samples (5 µl volume per sample) is collected at various time points, including 0, 5, 20, 40, 90 and 240 minutes. Concentrations are determined by measuring intrinsic fluorescence of each sodium channel blocker using a Fluorocount Microplate Flourometer or HPLC. Quantitative analysis employs a standard curve generated from authentic reference standard materials of known concentration and purity. Data analysis of the rate of disappearance is performed using nonlinear regression, one phase exponential decay (Prism V 3.0).

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

3. In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 µl KBR, containing 10 µM test compound) is placed on the epithelial lumenal surface. Sequential 5 to 10 µl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolities, and HPLC mobilities of novel metabolites are then performed.

4. Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

Methods

Animal Preparation:

Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-Aerosol:

Aerosols of $^{99m}$Tc-Human serum albumin (3.1 mg/ml; containing approximately 20 mCi) were generated using a Raindrop Nebulizer which produces a droplet with a median aerodynamic diameter of 3.6 µm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of Activity at t-Zero):

A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 Hours):

The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paried t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. All reagents and solvents were purchased from Aldrich Chemical Corp. and used without further purification. Proton and carbon NMR spectra were obtained on a Bruker AC 300 spectrometer at 300 MHz and 75 MHz, respectively. Proton spectra were referenced to tetramethylsilane as an internal standard and the carbon spectra were referenced to $CDCl_3$, $CD_3OD$, acetone-$d_6$ or DMSO-$d_6$ (purchased from Aldrich or Cambridge Isotope Laboratories, unless otherwise specified). Melting points were obtained on a Mel-Temp II apparatus and are uncorrected. ESI Mass spectra were obtained on a Shimadzu LCMS-2010 EV Mass Spectrometer. HLPC analyses were obtained using a Waters XTerra RP C18 Analytical Column detected at 220 nm (unless otherwise specified) on a Shimadzu Prominence HPLC system. With a flow rate of 1.0 mL per minute, the following time program was utilized:

| Time | Percent A ($H_2O$ with 0.05% TFA) | Percent B ($CH_3CN$ with 0.05% TFA) |
| --- | --- | --- |
| 0:00 | 90 | 10 |
| 20:00 | 10 | 90 |
| 30:00 | 10 | 90 |
| 35:00 | 90 | 10 |

The following definitions for abbreviations will apply unless otherwise indicated.

| Abbreviation | Definition |
| --- | --- |
| THF | tetrahydrofuran |
| Cbz | Benzyloxycarbonyl i.e. —(CO)O-benzyl |
| AUC | Area under the curve or peak |
| EtOAc | Ethyl acetate |
| $R_f$ | Retardation factor |
| HPLC | High performance liquid chromatography |
| MTBE | Methyl tertiary butyl ether |
| $t_R$ | Retention time |
| GC-MS | Gas chromatography-mass spectrometry |
| wt % | Percent by weight |
| h | hours |
| min | minutes |
| MHz | megahertz |
| MeOH | methanol |
| TFA | Trifluoroacetic acid |
| UV | Ultraviolet |

Preparation of Formula I (15)

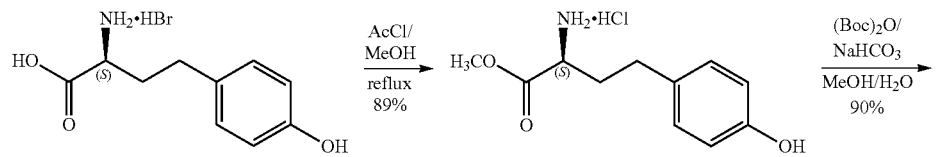

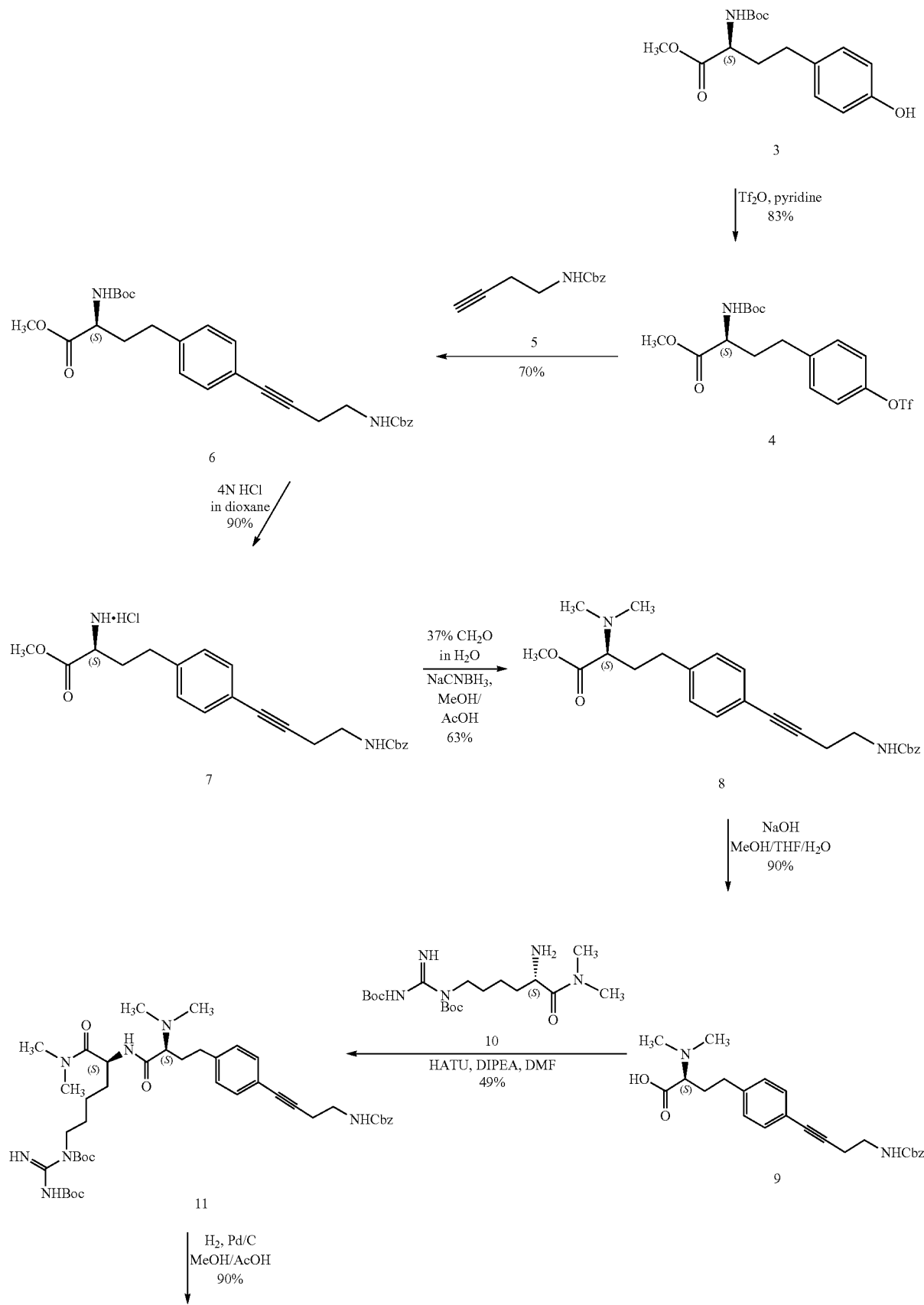

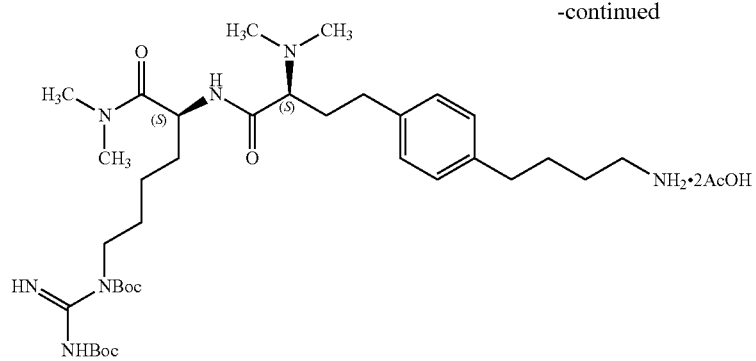
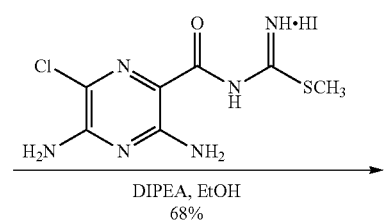
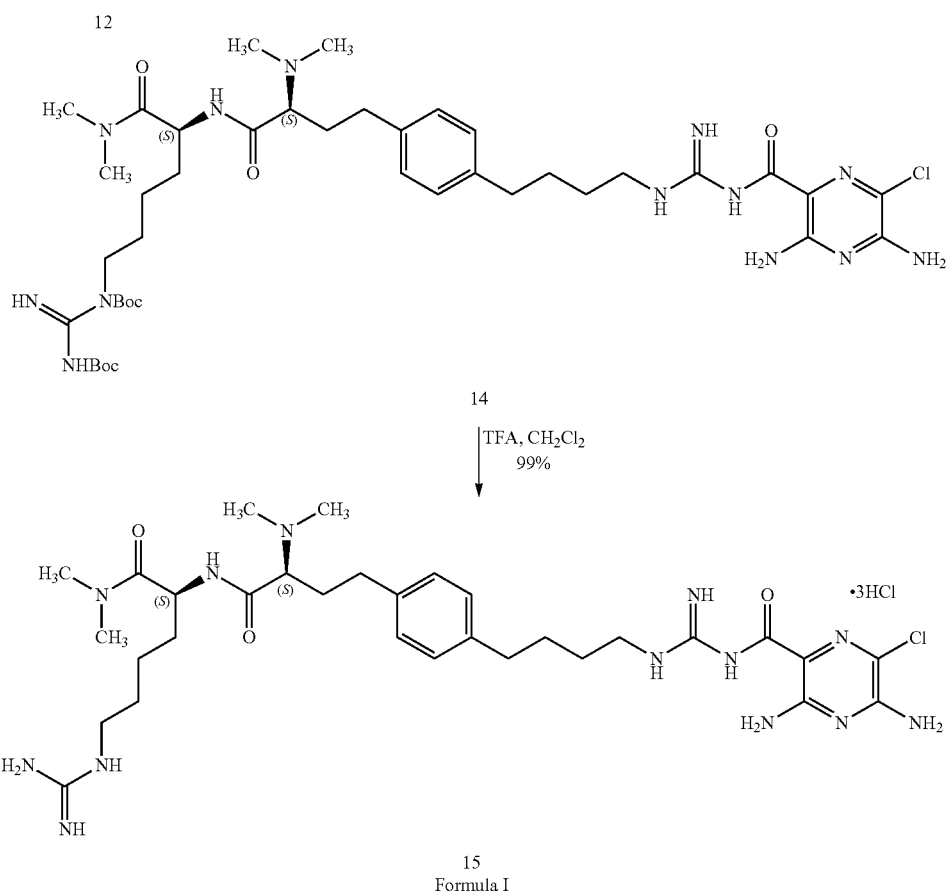

15
Formula I

Preparation of Compound 2

Acetyl chloride (27.1 mL, 380.1 mmol) was added drop wise to MeOH (225 mL) at room temperature, and compound 1 (15.0 g, 54.3 mmol) was added. The resulting solution was refluxed overnight and concentrated, then crashed from hexanes (700 mL) to afford desired compound 2 (14.0 g, 89%) as an off-white solid: $^1$H NMR (300 MHz, CD$_3$OD) δ 7.07 (d, J=8.7 Hz, 2H), 6.71 (d, J=8.7 Hz, 2H), 4.02 (t, J=6.6 Hz, 1H), 3.68 (s, 3H), 2.75-2.57 (m, 2H), 2.22-2.05 (m, 2H).

Preparation of Compound 3

To a solution of compound 2 (14.0 g, 48.2 mmol) in MeOH/H$_2$O (140 mL/70 mL) was added NaHCO$_3$ (28.5 g, 337.4 mmol) and Boc$_2$O (11.5 g, 53.0 mmol) at 0° C. The resulting mixture was allowed to warm to room temperature and stirred overnight. The reaction mixture was partitioned between EtOAc (300 mL) and water (300 mL) The aqueous layer was separated and extracted with EtOAc (2×300 mL). The combined organic extracts were washed with brine, dried over Na$_2$SO$_4$ and concentrated to give compound 3 (13.5 g, 90%) as an off-white solid: $^1$H NMR (300 MHz, CD$_3$OD) δ 6.98 (d, J=8.4 Hz, 2H), 6.67 (d, J=8.4 Hz, 2H), 4.03 (t, J=4.5 Hz, 1H), 3.68 (s, 3H), 2.65-2.40 (m, 2H), 1.92-1.82 (m, 1H), 1.44 (s, 9H).

Preparation of Compound 4

To a solution of compound 3 (13.5 g, 43.6 mmol) in pyridine (150 mL) was added triflate (7.3 mL, 43.6 mmol) at 0° C., and the reaction mixture was stirred at 0° C. for 3 h. After concentrated, the reaction mixture was partitioned between EtOAc (300 mL) and water (300 mL). The aqueous layer was separated and extracted with EtOAc (2×300 mL). The combined organic extracts were washed with brine, dried over $Na_2SO_4$ and concentrated. The residue was purified by column chromatography (silica gel, 95:5 $CHCl_3$/MeOH) to afford desired compound 4 (16.0 g, 83%) as an off brown solid: $^1H$ NMR (300 MHz, $CDCl_3$) δ 7.26-7.23 (m, 2H), 7.20-7.17 (m, 2H), 5.08 (br s, 1H), 4.36 (br s, 1H), 3.71 (s, 3H), 2.73-2.67 (m, 2H), 2.21-2.13 (m, 1H), 1.99-1.87 (m, 1H), 1.45 (s, 9H).

Preparation of Compound 6

To a solution of compound 4 (16.0 g, 36.2 mmol) in anhydrous $CH_3CN$ (160 mL) was added TEA (20.9 mL, 144.8 mmol), 10% (t-Bu)$_3$P in hexanes (1.4 g, 7.2 mmol), benzyl but-3-ynylcarbamate (5, 8.8 g, 43.4 mmol) and CuI (340 mg, 1.8 mmol) at room temperature. The resulting mixture was degassed with Argon for 3 min and $Pd(PPh_3)_4$ (4.1 g, 3.6 mmol) was added rapidly in one portion. After degassed with Argon for 5 min, the resulting mixture was heated at 60° C. for 12 h. The reaction mixture was concentrated in vacuum and the residue was purified by column (silica gel, 40:60 hexanes/EA) to afford compound 6 (16.0 g, 70%) as a brown oil: $^1H$ NMR (300 MHz, $CDCl_3$) δ 7.36-7.28 (m, 8H), 7.07 (d, J=8.4 Hz, 2H), 5.12 (br s, 4H), 4.33 (br s, 1H), 3.71 (s, 3H), 3.46-3.39 (m, 2H), 2.68-2.59 (m, 4H), 2.14-2.20 (m, 1H), 1.96-1.84 (m, 1H), 1.44 (s, 9H).

Preparation of Compound 7

Compound 6 (8.0 g, 16.1 mmol) was dissolved in 4 N HCl in dioxane (60 mL) at room temperature and the resulting solution was stirred for 1 h. After concentrated, the residue was crashed from MTBE to afford hydrochloric acid salt 7 (6.75 g, 90%) as a white solid: $^1H$ NMR (300 MHz, $CD_3OD$) δ 7.32-7.28 (m, 7H), 7.18 (d, J=8.1 Hz, 2H), 5.08 (s, 2H), 4.04 (t, J=6.3 Hz, 1H), 3.82 (s, 3H), 3.31-3.29 (m, 2H), 2.82-2.67 (m, 2H), 2.58 (t, J=6.9 Hz, 2H), 2.26-2.08 (m, 2H).

Preparation of Compound 8

To a solution of compound 7 (6.75 g, 15.6 mmol) in MeOH/AcOH (70 mL/15 mL) was added 37% $CH_2O$ in $H_2O$ (25.2 mL, 312 mmol) and sodium cyanoborohydride (7.84 g, 124.8 mmol). The reaction mixture was stirred at room temperature overnight. After concentrated, the residue was purified by column chromatography (silica gel, 10:1 $CH_2Cl_2$/MeOH, 10:1:0.1 $CHCl_3$/MeOH/$NH_4OH$) to afford desired compound 8 (3.8 g, 63%) as a off-white solid: NMR (300 MHz, $CDCl_3$) δ 7.36-7.26 (m, 7H), 7.11 (d, J=8.1 Hz, 2H), 5.11 (s, 2H), 3.69 (s, 3H), 3.45-3.39 (m, 2H), 3.10 (t, J=7.5 Hz, 1H), 2.65-2.60 (m, 4H), 2.32 (s, 6H), 2.01-1.88 (m, 2H).

Preparation of Compound 9

To a solution of methyl ester 8 (3.80 g, 8.9 mmol) in THF/MeOH/$H_2O$ (30 mL/30 mL/10 mL) was added NaOH (3.50 g, 89.0 mmol). The reaction mixture was stirred at room temperature overnight. After concentrated, the residue was dissolved in $H_2O$ (50 mL) and 1 N aq HCl was added to adjust pH value to 5. The resulting precipitate was filtered out and dried to afford desired compound 9 (3.25 g, 90%) as an off-white solid: NMR (300 MHz, $CD_3OD$) δ 7.32-7.28 (m, 7H), 7.17 (d, J=8.4 Hz, 2H), 5.08 (s, 2H), 3.46-3.42 (m, 1H), 3.45-3.39 (m, 2H), 2.83-2.70 (m, 8H), 2.58 (t, J=6.9 Hz, 2H), 2.15-2.05 (m, 2H).

Preparation of Compound 11

To a solution of compound 9 (1.80 g, 4.4 mmol) in anhydrous DMF (20 mL) was added HATU (3.3 g, 8.8 mmol) and DIPEA (4.0 mL, 22.0 mmol). The resulting solution was stirred at room temperature for 0.5 h and amine 10 (2.1 g, 5.2 mmol) was added. The reaction mixture was stirred at room temperature overnight and partitioned between EtOAc (200 mL) and water (200 mL). The aqueous layer was separated and extracted with EtOAc (2×200 mL). The combined organic extracts were washed with brine, dried over $Na_2SO_4$ and concentrated. The residue was purified by column chromatography (silica gel, 95:5 $CHCl_3$/MeOH) to afford desired compound 11 (1.70 g, 49%) as a white solid: $^1H$ NMR (300 MHz, $CDCl_3$) δ 7.36-7.28 (m, 7H), 7.10 (d, J=8.1 Hz, 2H), 5.10 (s, 3H), 4.97-4.90 (m, 1H), 3.86 (t, J=6.6 Hz, 2H), 3.45-3.35 (m, 2H), 3.12 (s, 3H), 3.09-3.00 (m, 2H), 2.96 (s, 3H), 2.91-2.71 (m, 2H), 2.62 (t, J=6.3 Hz, 2H), 2.30 (s, 6H), 1.97-1.31 (m, 26H).

Preparation of Compound 12

A suspension of compound 11 (1.7 g, 2.1 mmol) and 10% Pd/C (800 mg) in MeOH/AcOH (25 mL/1.0 mL) was subjected to hydrogenation conditions (1 atm) overnight at room temperature. The reaction mixture was filtered through celite and washed with MeOH. The filtrate was concentrated in vacuum and crashed from MTBE to afford acetic salt 12 (1.45 g, 90%) as colorless oil: $^1H$ NMR (400 MHz, $CD_3OD$) δ 7.12 (s, 4H), 4.97-4.90 (m, 2H), 3.90-3.85 (m, 2H), 3.29 (s, 3H), 2.95 (s, 3H), 2.91 (t, J=7.6 Hz, 2H), 2.63 (t, J=6.8 Hz, 2H), 2.57-2.50 (m, 8H), 1.95 (s, 6H), 2.02-1.96 (m, 2H), 1.80-1.62 (m, 10H), 1.50 (s, 9H), 1.45 (s, 9H).

Preparation of Compound 14

To a solution of acetic acid salt 12 (1.45 g, 2.1 mmol) and methyl 3,5-diamino-6-chloropyrazine-2-carbonylcarbamimidothioate hydroiodic acid salt (13, 1.28 g, 3.3 mmol) in EtOH (20 mL) was added DIPEA (2.17 g, 16.8 mmol) at room temperature. The reaction mixture was heated at 70° C. for 2 h, then cooled to room temperature and concentrated in vacuum. The residue was purified by column chromatography (silica gel, 9:1 $CH_2Cl_2$/MeOH, 80:18:2 $CHCl_3$/MeOH/$NH_4OH$) to afford desired compound 14 (1.15 g, 68%) as a yellow solid: $^1H$ NMR (400 MHz, $CD_3OD$) δ 7.09 (s, 4H), 4.87-4.82 (m, 2H), 3.86 (t, J=7.2 Hz, 2H), 3.24-3.18 (m, 3H), 3.22 (s, 3H), 2.96-2.91 (m, 4H), 2.64-2.47 (m, 4H), 2.30 (t, 6H), 1.99-1.72 (m, 10H), 1.55-1.32 (m, 20H).

Preparation of Compound 15 [Formula I]-3,5-diamino-6-chloro-N—(N-(4-(4-((S)-3-(dimethylamino)-4-((S)-1-(dimethylamino)-6-guanidino-1-oxohexan-2-ylamino)-4-oxobutyl)phenyl)butyl)carbamimidoyl)pyrazine-2-carboxamide To a solution of compound 14 (670 mg, 0.7 mmol) in $CH_2Cl_2$ (20 mL) was added TFA (5.0 mL) and the resulting solution was stirred at room temperature for 2 h. The reaction mixture was concentrated in vacuum and azeotroped with 1 N aq HCl for 3 times to afford hydrochloric acid salt of 15 (Formula I, 600 mg, 99%) as a yellow hygroscopic solid: $^1H$ NMR (400 MHz, $D_2O$) δ 7.16-7.15 (m, 4H), 3.84-3.81 (m, 1H), 3.26 (br s, 2H), 3.13-3.11 (m, 5H), 2.91-2.86 (m, 9H), 2.61-2.53 (m, 4H), 2.25-2.11 (m, 2H), 1.74-1.23 (m, 10H).

Summary of in vitro data for Compound 15:
- Potency ($IC_{50}$) on Canine Bronchial Epithelial Cells: 5.3±3.3 nM (n=5) (FIG. 1)
- Reversal of Maximal Effect on Canine Bronchial Epithelial Cells: 6.8±5.1% (n=3) of effect was lost with 3 washes
- Absorption Rate Across Human Bronchial Epithelial Cells: 0.12±0.05 $nM/cm^2/min$ (n=3)
- Metabolism by Human Bronchial Epithelial: No metabolites detected apical or basolateral
- Human Plasma Stability: No metabolism detected over 4 hours
- Durability of Retention of Airway Surface Liquid by Canine Bronchial Epithelial Cells: 94±5% (n=3) of fluid retained 8 hours after drug delivery; 56±6% (n=2) of fluid retained 24 hours after drug delivery
- Rat Hepatocyte Metabolism: No evidence of significant metabolism throughout 24-hour incubation
- Human Plasma Protein Binding: 80±5% (n=6) bound to plasma proteins A Dose Response Curve of ENaC Inhibition with P-1046 (I) and Amiloride is shown in FIG. 1.

Figure 2A:
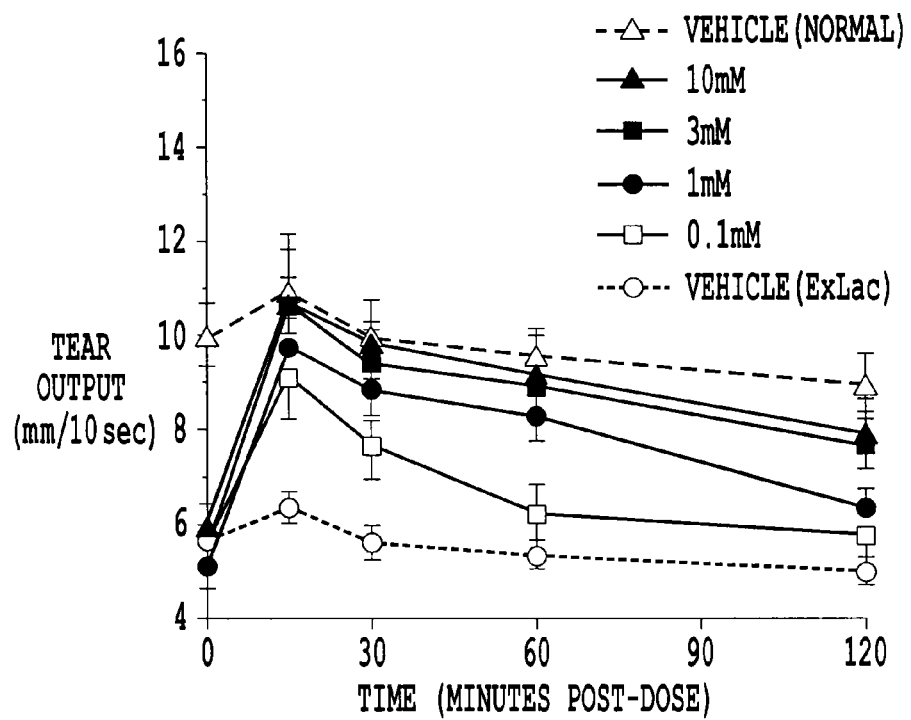
FIG. 2: The Effects of P-1046 (Formula I, 15) Concentration on Tear Output in ExLac Rats. The raw PRT tear output values are shown in the left panel and the baseline corrected values are shown in the right panel. At all concentrations, P-1046 increases tear output in ExLac rats 15 minutes post-dose at or slightly below tear output values observed for normal rats. The effects are still observed 2 hours post-dose, with the exception of the 0.1 mM dose group. n=4 for all groups.
Figure 2B:
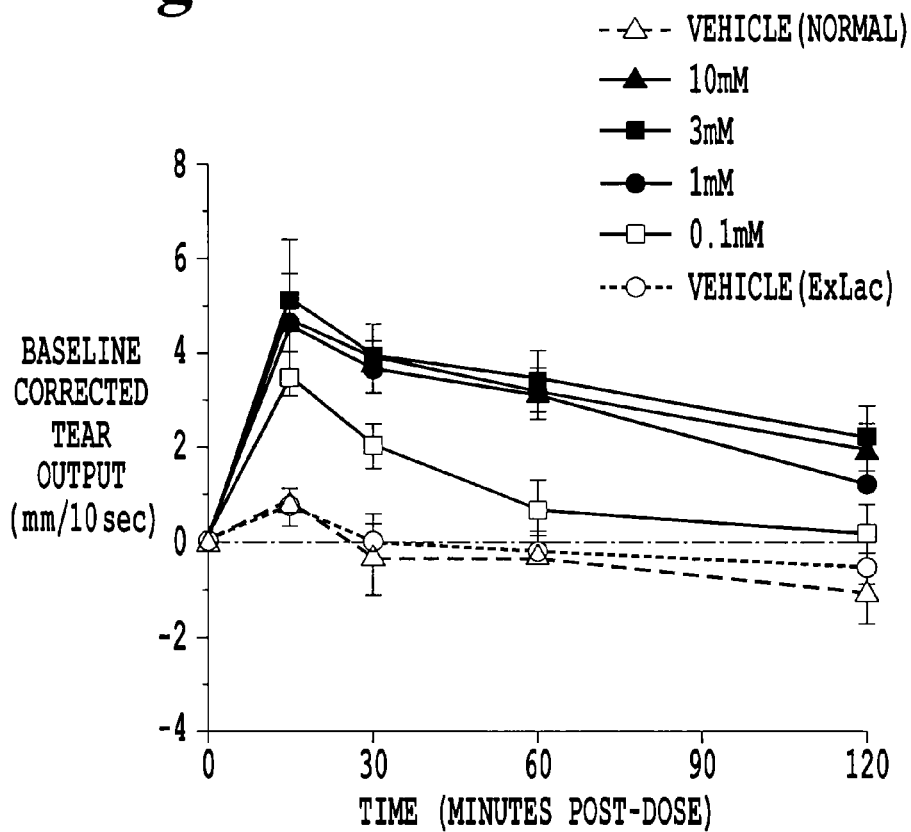

Ocular Data and Methods for Compound 15 (Formula I, aka I, aka P-1046, aka 1046):

The Effects of P-1046 (Formula I, 15) Concentration on Tear Output in ExLac Rats is shown in FIG. 2

Figure 3:
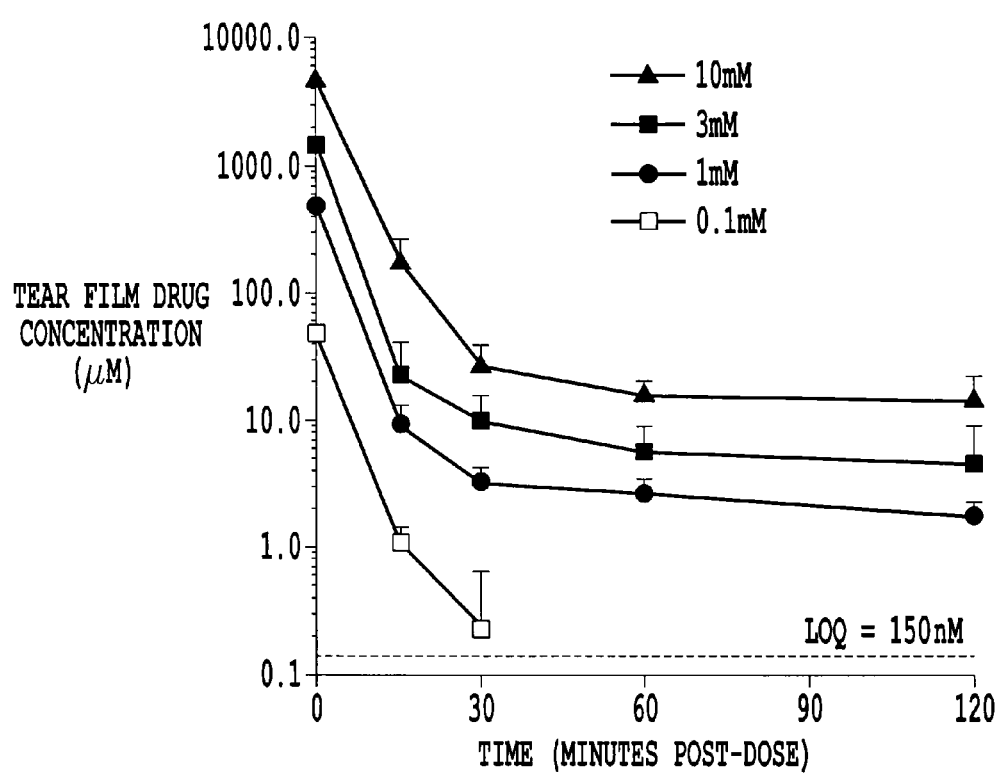
FIG. 3: The Clearance of P-1046 (Formula I, 15) from the Ocular Surface. The concentration of P-1046 was determined using the procedures described above by determining the mass of P-1046 extracted from each thread and determining the concentration based on the volume of fluid wicked onto the thread. For all concentrations tested, P-1046 exhibits an apparent bi-phasic clearance, whereby the majority of the drug is cleared from the ocular surface by 30 minutes post-dose, followed by a slow clearance phase from 30 to 120 minutes post-dose. Note, the concentration of P-1046 during the slow clearance phase for concentration ≥1 mM are well above the IC50 for P-1046 (5.3 nM), thereby providing the long lasting increase in tear volume.

The Clearance of P-1046 (Formula I, 15) from the Ocular Surface is shown in FIG. 3.

Figure 4A:
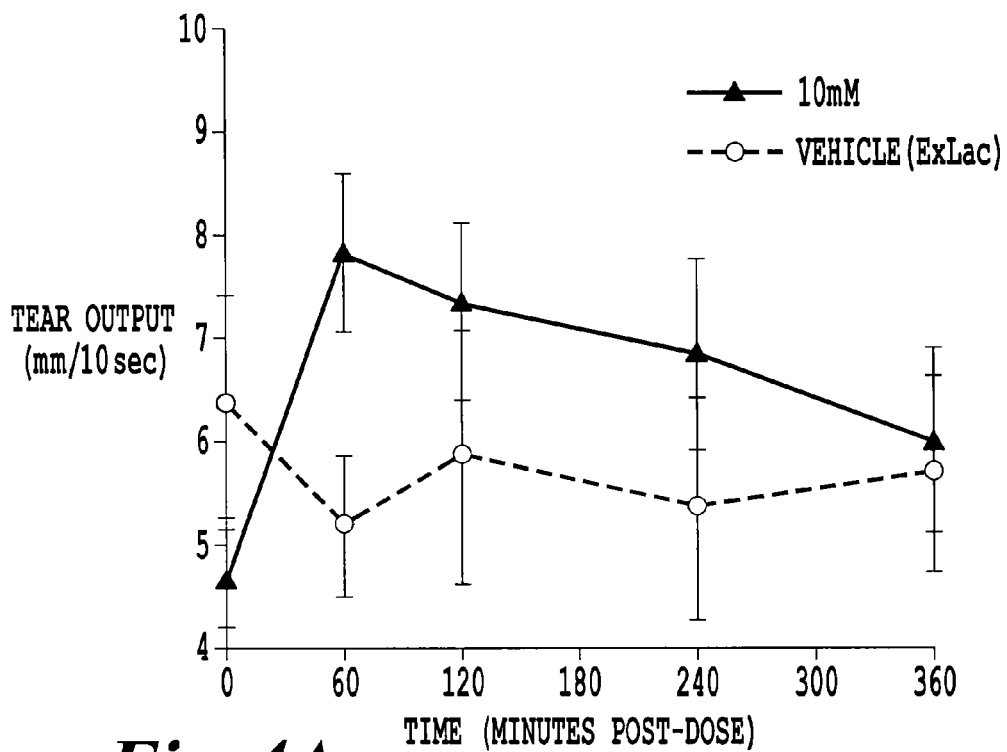
FIG. 4.
Figure 4B:
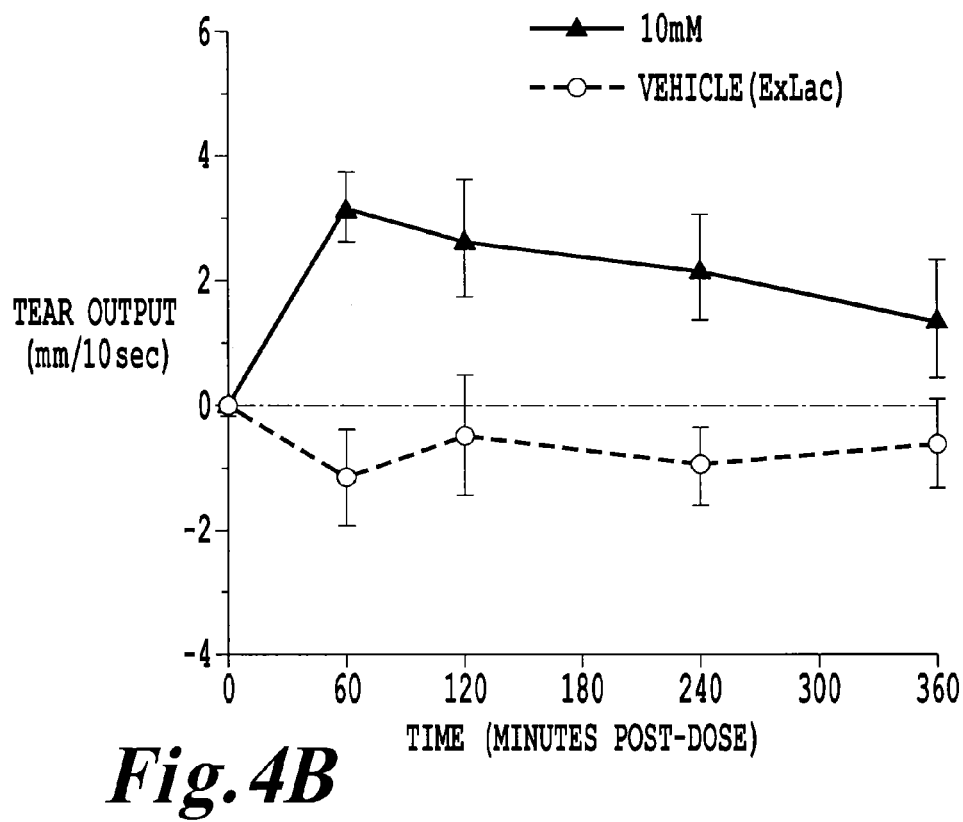

The Effects of 10 mM P-1046 (Formula I, 15) on Tear Output in ExLac Rats is shown in FIG. 4.

Procedures for Phenol Red Thread (PRT) Measurement of Tear Output:

Animal Species/Strain: Rats, Sprague Dawley (SD); Lacrimal gland surgically removed (ExLac).

Animal Number/Sex: 3-4 females/group

Test Article Formulation: All stock solutions for each dosing arm were prepared no more than 48 hours prior to the start of the study. The concentration of ENaC blockers in all test article solutions were confirmed by spectrophotometry.

Test Article Administration: Both the ipsilateral and contralateral eyes were dosed with 5 □l of test article solution.

Phenol Red Thread (PRT) Test: Tear production was measured using the ZoneQuick cotton thread with impregnated phenol red dye. The folded end of the thread was held in the lateral-ventral conjunctival cul-de-sac for 10 seconds. The length of tear wicking onto the thread was determined by measuring the length of the thread that changes color from yellow to red. Use of a stereomicroscope was assist in the accurate measurement (recorded in millimeters) of the wicking/color change.

Procedure for P-1046 (Compound 15 Formula I, aka I, aka P-1046, aka 1046): Extraction from PRT Threads:

All PRT threads were collected in eppendorf tubes and stored at −20 C until the time of drug concentration analysis. P-1046 was extracted from threads and analyzed as follows:

1. 200 μL of 70% ACN (70% ACN, 30% $H_2O$) was added into sample tubes which have threads in them.
2. Tubes from Step 1 were vortexed for 30 seconds and sonicated for 1 minute to fully immerse the threads.
3. The sample solutions were incubated for 4 hours at room temperature.
4. Samples were vortexed again for 30 seconds.
5. 75 μL of the each sample solution (from step 4) was removed into 96-well UPLC plate with an additional 75 μL of mobile phase A (5 mM ammonium formate, 0.1% formic acid in $H_2O$) added into each sample well.
6. Analytical standards (10 mM, 1 mM, 100 □M, 10 □M, 1 □M, 100 nM, Buffer) were prepared identically to the thread solutions.
7. Drug concentrations from all samples were analyzed by UPLC.

Solubility and Stability Testing for Compound 15 (Formula I, aka I, aka P-1046, aka 1046):

Procedure for Solubility and Stability Evaluation:

1. Prepare 2.8% NaCl and 25 mM citrate buffer, pH of the solution 4.2. The osmolality of the solution is approximately 940 mOsM.
2. Add appropriate amount of buffer solution to a test compound to make approximate concentration of 10 mg/mL.
3. Vortex the solution for 15 seconds, sonicate for 30 seconds, again vortex for 60 seconds and visually observe the solution.
4. Calculate final concentration of the solution by a spectrophotometer.
   Remove a portion of solution and dilute it to 1:10 ratio. Put this solution at 50° C. for the accelerated stability study for 10 days.
   Obtain stability data by HPLC analysis
5. Prepare 2.8% NaCl and 25 mM citrate buffer, pH of the solution 4.2. The osmolality of the solution is approximately 940 mOsM.
6. Add appropriate amount of buffer solution to a test compound to make approximate concentration of 10 mg/mL.
7. Vortex the solution for 15 seconds, sonicate for 30 seconds, again vortex for 60 seconds and visually observe the solution.
8. Calculate final concentration of the solution by a spectrophotometer.
   Remove a portion of solution and dilute it to 1:10 ratio. Put this solution at 50° C. for the accelerated stability study for 10 days.
   Obtain stability data by HPLC analysis.

Figure 5A:
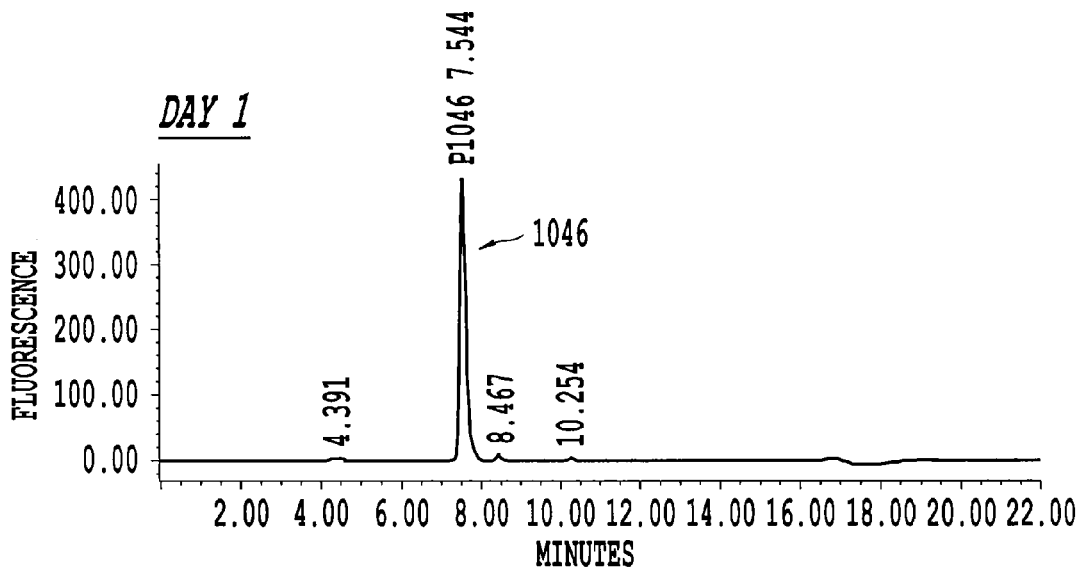
FIG. 5: HPLC Analysis of P-1046 (Formula I, 15) solubility/stability samples at Day 1 and Day 10. No degradation of P-1046 was observed after 10 days at 50° C. in pH 4.2 citrate buffer with 2.8% NaCl. P-1046 was fully soluble in this buffer at the highest concentration tested 8.8 mg/mL.
Figure 5B:
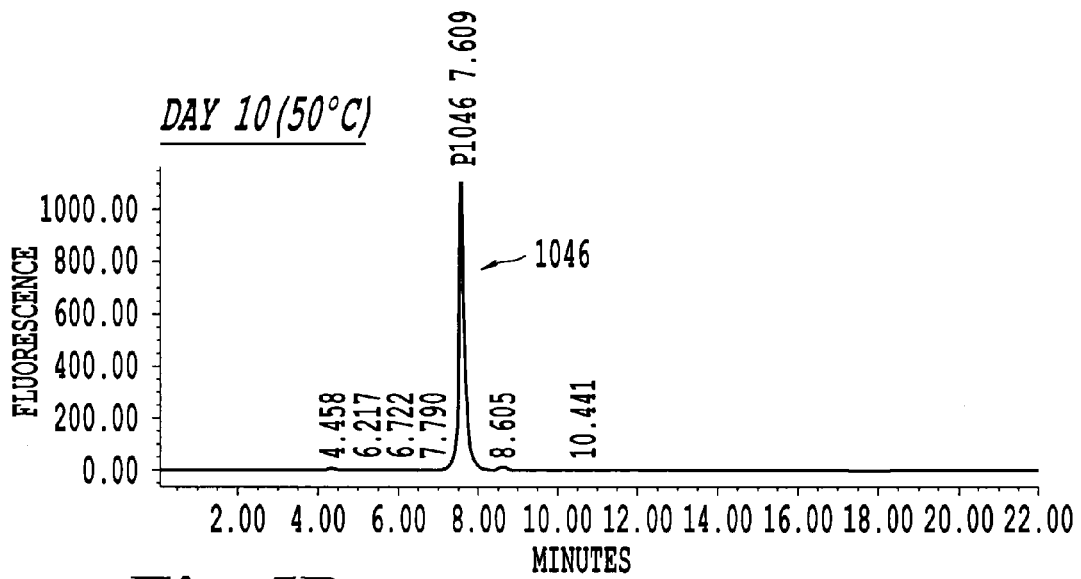

FIG. 5 shows HPLC Analysis of P-1046 (Formula I, 15) solubility/stability samples at Day 1 and Day 10.

Summary Safety and Tolerability for Compound 15 (Formula I, aka I, aka P-1046, aka 1046):

An Acute Non-GLP Ocular Toxicity Study in New Zealand White Rabbits with P-1046

Objective:

The purpose of this study was to evaluate the ocular tolerability and systemic exposure of P-1046, an inhibitor of the epithelial sodium channel (ENaC), when administered as a topical instillation to New Zealand white rabbits.

Methods:

The test article (P-1046) were supplied as a light yellow white powder. The test articles were then prepared into dosing solutions for topical ocular application. Twenty-eight experimentally naïve male New Zealand White rabbits, approximately 4 months old at the outset of the study and weighing 2.6-3.1 kilograms at randomization were assigned to treatment groups as shown in the table below:

| Group | P-1046 Concentration (Right Eye)* | Number of doses** | Number of Animals |
|---|---|---|---|
| 1. Vehicle | 0 | 8 | 4 |
| 6. P-1046 - low dose | 10 | 8 | 4 |
| 7. P-1046 - high dose | 30 | 4 | 4 |

*At each dose, 50 µl of vehicle or test article solution was instilled onto the right eye and 50 µl of saline was instilled onto the left eye
**Doses were administered eight times (1 hr between doses, 10 mM dose groups) or four times (2 hr between each dose, 30 mM dose groups) during a single day Animals were administered 50 µl of the test or control vehicle onto the globe of right eye and 50 µl of saline onto the globe of the left eye eight times (approximately one hour between each dose) in Groups 1 and 6 and four times (approximately two hours between each dose) in Group 7. Mortality and clinical observations were recorded daily. Body weights were recorded at randomization/selection and prior to sacrifice on Day 2. For blink rate assessment, eye blinks in the right eye only were counted for 3 minutes prior to treatment initiation and following all doses. Instances of wincing and pawing at the eyes during the 3-minute eye blink observation period were recorded as clinical observations. Food consumption was recorded daily. Eyes were scored according to Draize prior to treatment, following each dose and on Day 2 at approximately 24 hours post-dose. Blood for toxicokinetic evaluation was collected from animals in Group 2-7 at pre-dose, 30 minutes after the middle dose ($4^{th}$ dose in groups 3, 5, and 6; $2^{nd}$ dose in groups 2, 4, and 7) and at 30, 60, 120 and 240 minutes following the final dose on Day 1. Blood samples for evaluation of serum chemistry parameters were collected prior to treatment initiation and at 120 and 240 min following the final dose. Urine samples were collected over a 4-hour period following the final dose. All animals were sacrificed following completion of study procedures on Day 2.

Results and Conclusions:
Animals on study appeared to be in good overall health, as judged by clinical observations, body weights and food consumption.

Ocular irritation was assessed by blink rate measurement, Draize evaluation of the eyes and clinical observations. Irritation associated with each treatment is discussed below.

Vehicle

Figure 6A:
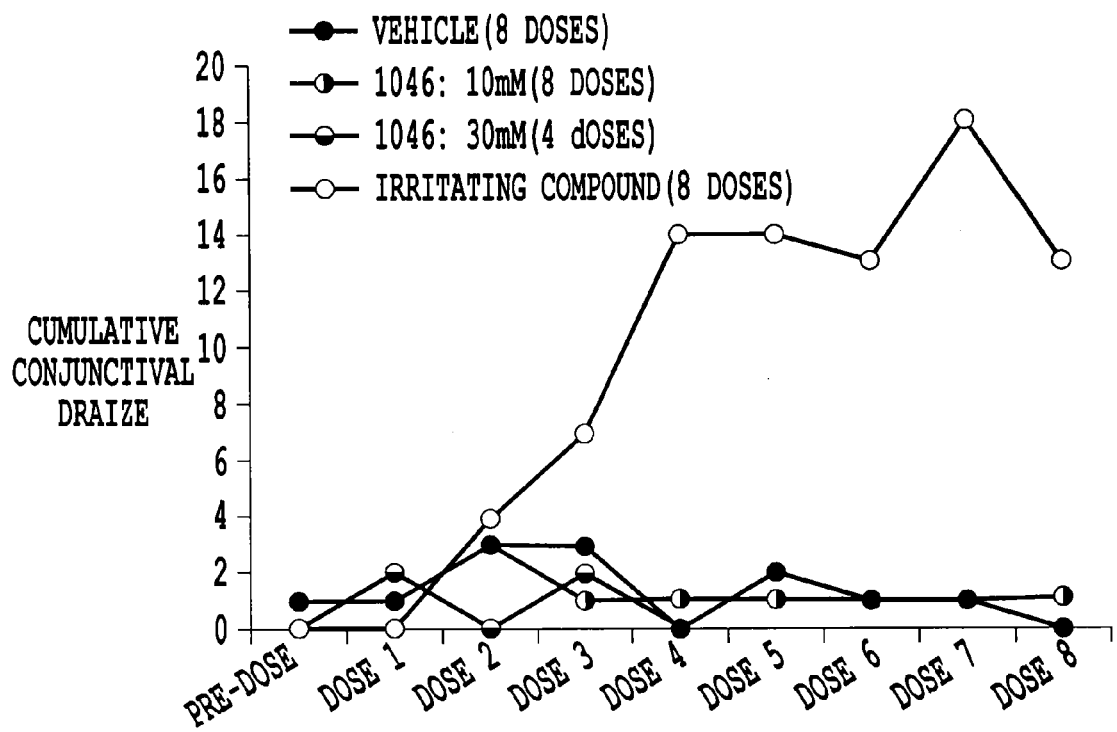
FIG. 6: Summary of P-1046 Ocular Tolerability. (A) The cumulative Draize scores for each dose group and each dosing interval (the data are the sum of all Draize scores for the right eye). Both dosing regimens for P-1046 show only slight increases in Draize scoring which are not greater than those observed for vehicle treated animals. For comparison, a compound identified as irritating in the same study is shown in yellow. (B) The average blink rate for each dose group at each dosing interval. Both dosing regimens for P-1046 show only slight increases at some time points, similarly to vehicle treated animals. These data suggest that P-1046 at 10 and 30 mM do not cause stinging on installation.
Figure 6B:
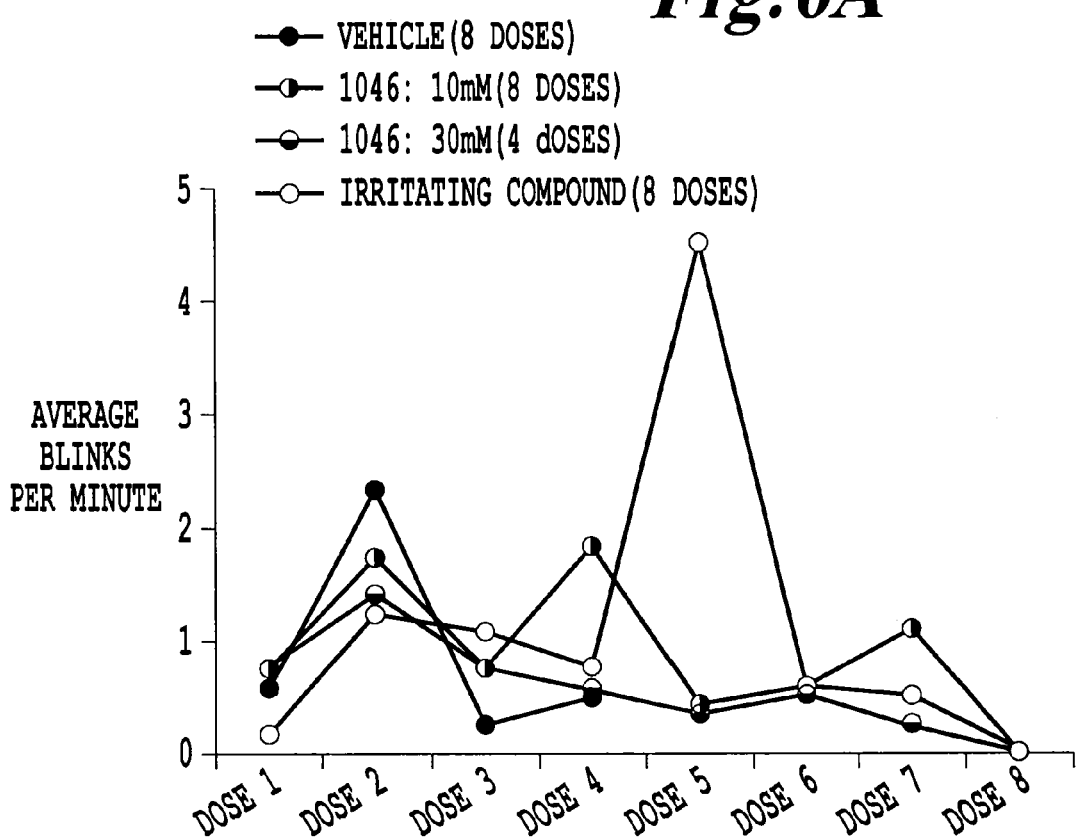

The vehicle was well tolerated with only minor, transient ocular irritation following dosing. The vehicle control animals had conjunctival redness in both eyes (max Draize score=1) and isolated incidences of wincing and pawing at the eyes. The incidence of conjunctival redness was slightly higher in eyes treated with vehicle (right eye), as compared to the eyes treated with saline (left eye), which suggests that observed irritation may have been the result of both vehicle effects and the dosing procedure (FIG. 6). All eyes appeared normal on Day 2.

10 and 30 mM P-1046

The P-1046 formulations were well tolerated. Post-dose conjunctival redness was observed, but the severity and incidence of this sign were comparable to the vehicle controls. All eyes in the 10 mM group appeared normal on Day 2.

A Summary of P-1046 Ocular Tolerability is shown in FIG. 6.

Figure 7A:
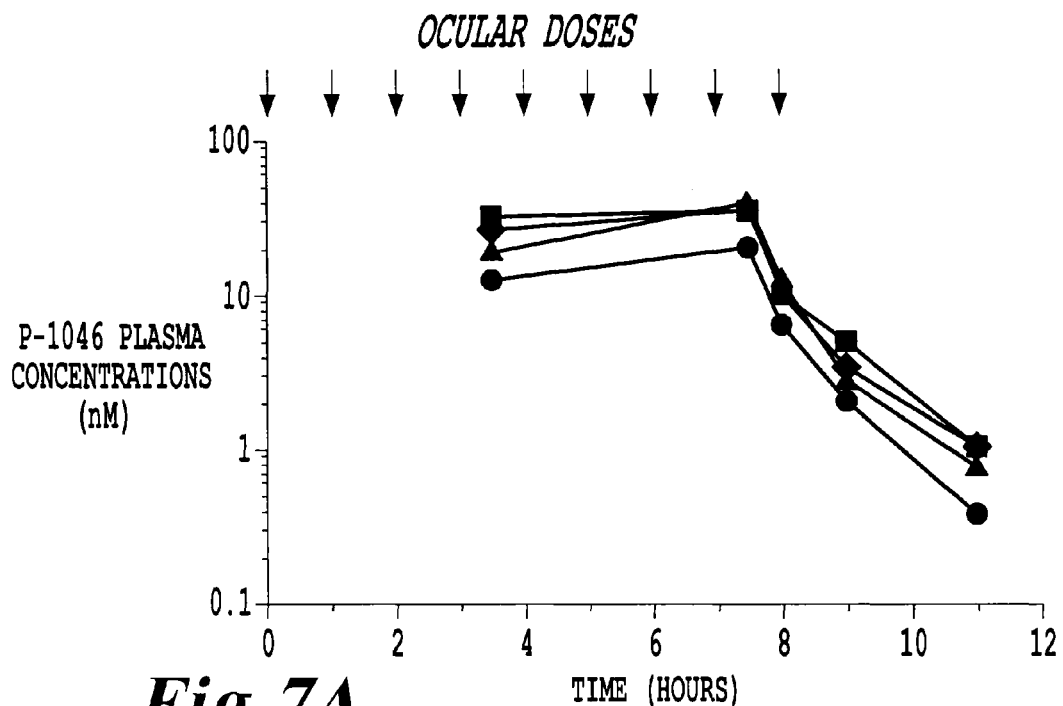
FIG. 7: P-1046 Plasma Levels after Ocular Dosing. (A) The plasma levels from individual animals during and after 8 doses of 10 mM P-1046 (50 ul/dose). (B) The plasma levels from individual animals during and after 4 doses of 30 mM P-1046 (50 ul/dose).
Figure 7B:
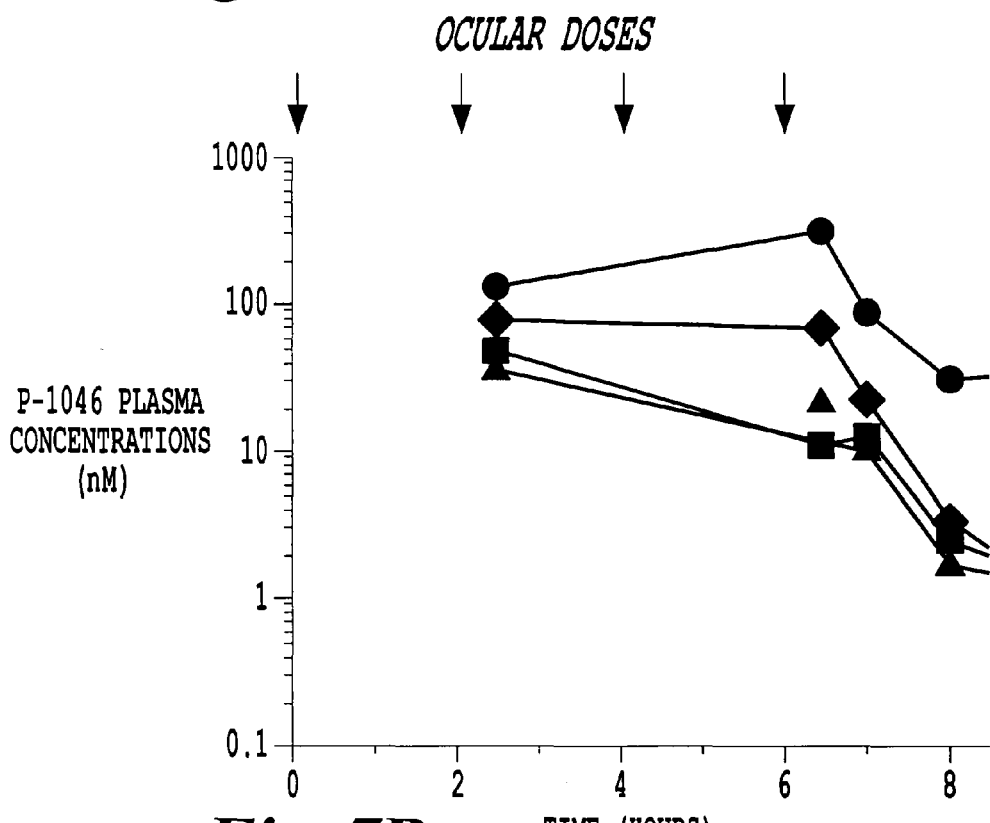

FIG. 7 shows P-1046 Plasma Levels after Ocular Dosing.

What is claimed is:
1. A compound represented by the formula (I):

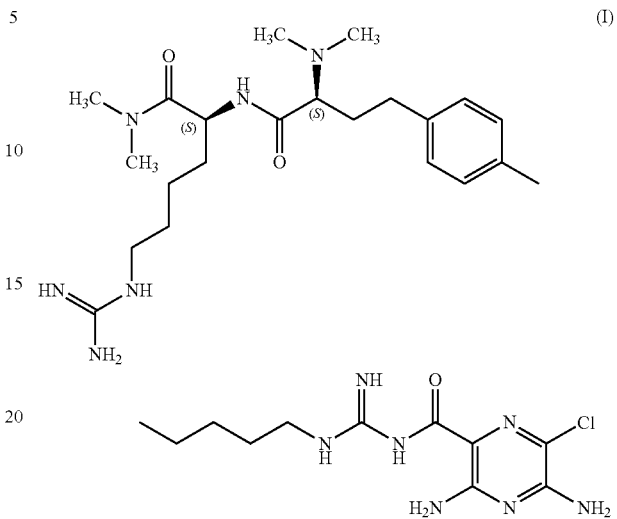

and racemates, enantiomers, diastereomers, tautomers, polymorphs, pseudopolymorphs and pharmaceutically acceptable salts, thereof.

2. The compound of claim 1, which is an acid addition salt of an inorganic acid or an organic acid selected from the group consisting of hydrochloric acid, hydrobromic acid, sulfuric acid, phosphoric acid, nitric acid, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalensulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, and lactic acid.

3. A pharmaceutical composition, comprising the compound of claim 1 and a pharmaceutically acceptable carrier.

4. A composition, comprising:
the compound of claim 1; and
a P2Y2 receptor agonist.

5. A composition, comprising:
the compound of claim 1; and
a bronchodilator.

6. A method of promoting hydration of mucosal surfaces, comprising:
administering an effective amount of the compound of claim 1 to a mucosal surface of a subject.

7. A method of blocking sodium channels, comprising:
contacting sodium channels with an effective amount of the compound of claim 1.

8. A method of treating a disease ameliorated by increased mucociliary clearance and mucosal hydration comprising administering to a subject in need of increased mucociliary clearance and mucosal hydration an effective amount of an osmolyte and the compound of claim 1.

9. The method of claim 8, wherein the compound is administered preceding administration of the osmolyte.

10. The method of claim 8, wherein the compound is administered concurrent with administration of the osmolyte.

11. The method of claim 8, wherein the compound is administered following administration of the osmolyte.

12. The method of claim 8, wherein the osmolyte is hypertonic saline or mannitol.

13. The method of claim 8, wherein the osmolyte is sodium chloride which is delivered as a micronized particle of respirable size.

14. The method of claim 8, wherein the effective amount of an osmolyte and a sodium channel blocker is administered by aerosolization using a device capable of delivering the formulation to the nasal passages or pulmonary airway wherein the aerosol is a respirable size.

15. A composition, comprising:
   (a) the compound of claim 1 and (b) an osmotically active compound.

16. A method of inducing sputum, comprising administering to a subject in need of increased mucociliary clearance and mucosal hydration an effective amount of an osmolyte and the compound of claim 1.

* * * * *

UNITED STATES PATENT AND TRADEMARK OFFICE
CERTIFICATE OF CORRECTION

PATENT NO. : 9,072,738 B2
APPLICATION NO. : 14/129734
DATED : July 7, 2015
INVENTOR(S) : Michael Ross Johnson Page 1 of 4

It is certified that error appears in the above-identified patent and that said Letters Patent is hereby corrected as shown below:

Title Page, Item (57)

In the Abstract at line 2:

"formula:" should read --formula (I) below.--

In the Abstract, after the text, the chemical structure of formula (I):

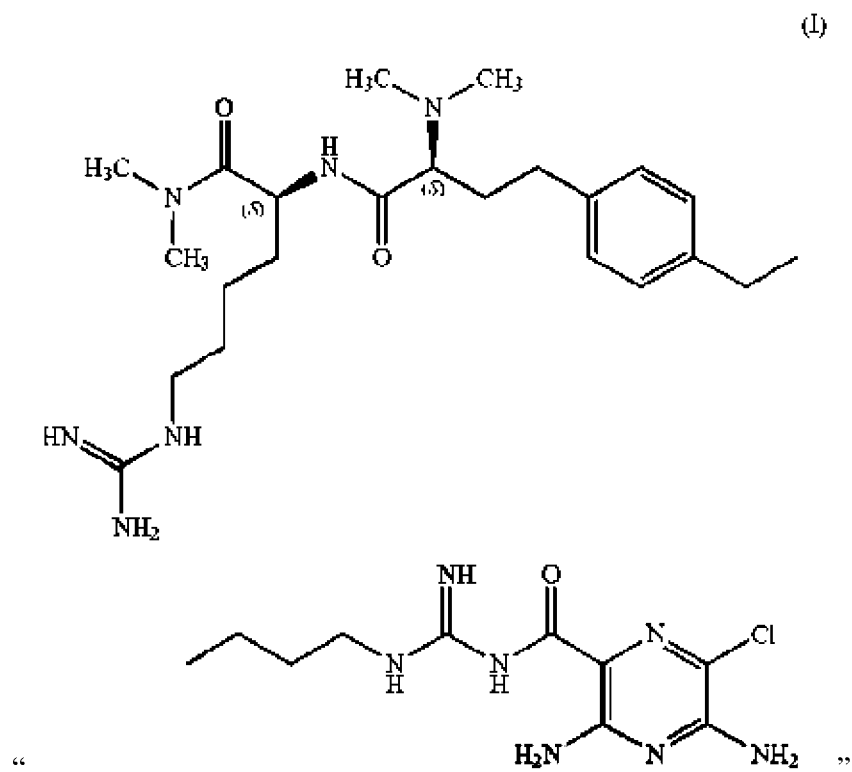

Signed and Sealed this
Twelfth Day of January, 2016

Michelle K. Lee
*Director of the United States Patent and Trademark Office*

CERTIFICATE OF CORRECTION (continued)
U.S. Pat. No. 9,072,738 B2

Should read

-- 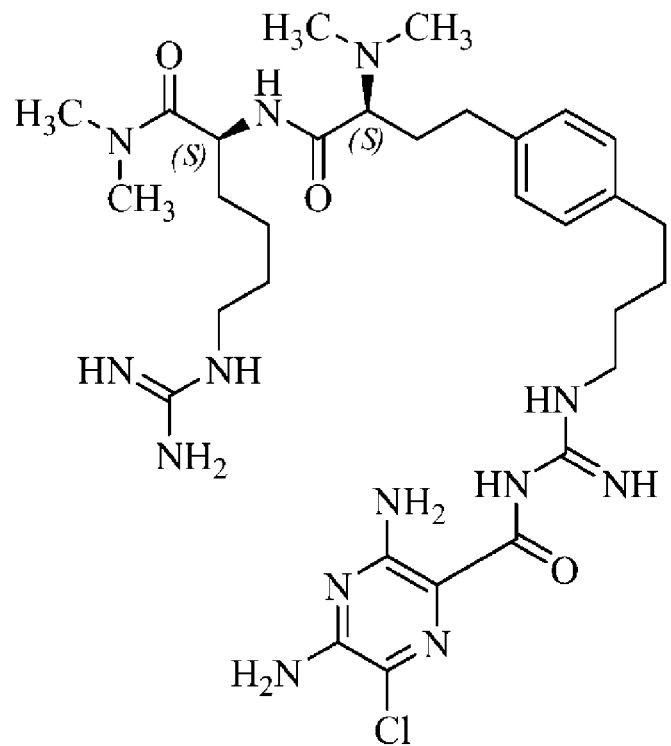

(I) --.

CERTIFICATE OF CORRECTION (continued)
U.S. Pat. No. 9,072,738 B2

In the Claims

In Claim 1, line 2, the chemical structure of formula (I):

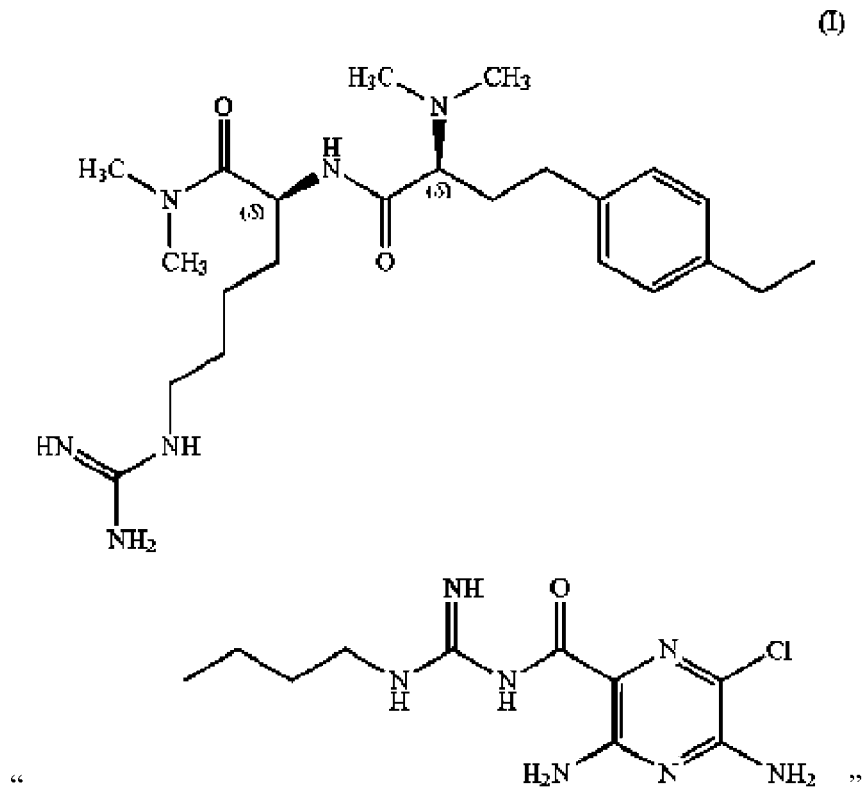

CERTIFICATE OF CORRECTION (continued)
U.S. Pat. No. 9,072,738 B2

Should read

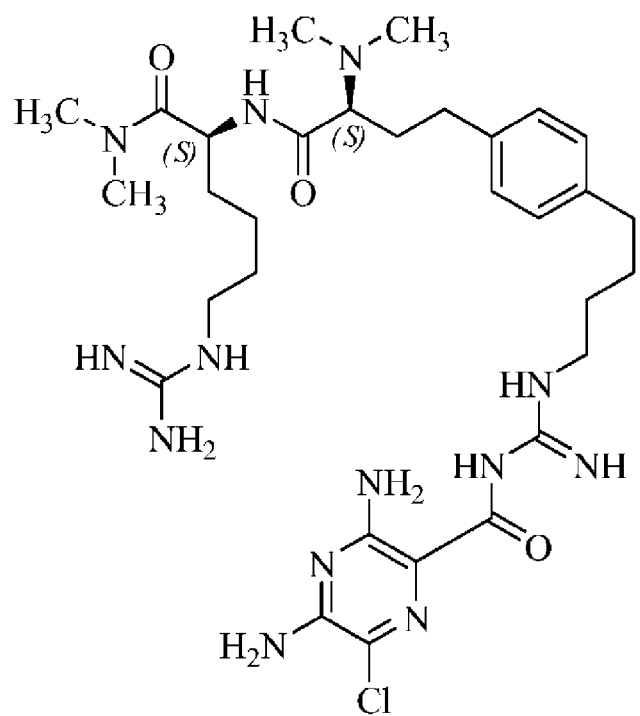

-- (I) --.